(12) United States Patent
Yang

(10) Patent No.: US 7,479,374 B2
(45) Date of Patent: Jan. 20, 2009

(54) TRIACYLGLYCEROL-DEFICIENT FISSION YEAST AND ITS USES

(75) Inventor: Hongyuan Yang, Singapore (SG)

(73) Assignee: National University of Singapore, Singapore (SG)

( * ) Notice: Subject to any disclaimer, the term of this patent is extended or adjusted under 35 U.S.C. 154(b) by 376 days.

(21) Appl. No.: 10/564,266

(22) PCT Filed: Jul. 9, 2004

(86) PCT No.: PCT/SG2004/000205

§ 371 (c)(1),
(2), (4) Date: Jul. 21, 2006

(87) PCT Pub. No.: WO2005/005617

PCT Pub. Date: Jan. 20, 2005

(65) Prior Publication Data

US 2007/0128605 A1 Jun. 7, 2007

Related U.S. Application Data

(60) Provisional application No. 60/485,385, filed on Jul. 9, 2003.

(51) Int. Cl.
*G01N 33/53* (2006.01)
*G01N 33/567* (2006.01)
*C12Q 1/68* (2006.01)
*C12N 15/00* (2006.01)

(52) U.S. Cl. ............................. 435/7.2; 435/6; 435/7.31

(58) Field of Classification Search ........................ None
See application file for complete search history.

(56) References Cited

FOREIGN PATENT DOCUMENTS

WO WO00/060095 A2 10/2000

OTHER PUBLICATIONS

Zhang et al. Schizosaccharomyces pombe cells deficient in triacylglycerols synthesis undergo apoptosis upon entry into the stationary phase. J. Biol. Chem. 278(47): 47145-55, 2003.*
Zhang, Q., et al. *Schizosaccharomyces pombe* Cells Deficient in 'Triacylglycerols Synthesis Undergo Apoptosis upon Entry into the Stationary Phase' The Journal of Biological Chemistry 278(47):47145-55. Sep. 8, 2003.
Dahlqvist, A., et al. Phospholipid:diacylglycerol acyltransferase: An enzyme that catalyzes the acyl-CoA-independent formation of triacylglycerol in yeast and plants' Proceedings of the National Academy of Science 97 (12):6487-92. Jun. 6, 2000.
GenBank Accession No. CAA2119; Apr. 16, 2005.
GenBank Accession No. CAA22887; Apr. 16, 2005.

* cited by examiner

*Primary Examiner*—David Guzo
*Assistant Examiner*—Michele K. Joike
(74) *Attorney, Agent, or Firm*—Townsend and Townsend and Crew LLP

(57) ABSTRACT

A fission yeast having non-functional dga1 and plh1 genes, which is incapable of synthesizing triacylglycerols, is disclosed. The fission yeast is susceptible to lipotoxicity including lipoapoptosis, and is useful for screening of compounds that inhibit or prevent lipotoxicity or lipoapoptosis. The fission yeast strain may be transformed to express a mammalian enzyme involved in triacylglycerol synthesis, and therefore is also useful for screening of compounds that inhibit or prevent triacylglycerol synthesis, which activity is conferred by the mammalian enzyme.

48 Claims, 16 Drawing Sheets

WT

DKO

SEQUENCE LISTING

<160> NUMBER OF SEQ ID NOS: 24

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer PLH1-55

<400> SEQUENCE: 1
ggggtaccac accctatttg caaca                                          25

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:PCR
      amplification primer PLH1-53

<400> SEQUENCE: 2
ccgctcgagg aattgcttga gcagcaac                                       28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:PCR
      amplification primer PLH1-35

```
<400> SEQUENCE: 3
cgggatcccg acaaacgaat atgataaa                                    28

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:PCR
      amplification primer PLH1-33

<400> SEQUENCE: 4
gctctagagg ctccatagaa ggtgaag                                     27

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:primer DGA1-
      55

<400> SEQUENCE: 5
ggggtaccga atccatgggt agtgat                                      26

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:primer DG11-
      53

<400> SEQUENCE: 6
ccgctcgagc ccgttctata taatcgt                                     27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:primer DGA1-
      35

<400> SEQUENCE: 7
cgggatccct tattggccta tgcaata                                     27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:primer DGA1-
      33

<400> SEQUENCE: 8
gctctagact gaatgaatat tagtaacgc                                   29

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:PCR
      amplification primer pca15
```

-continued

```
<400> SEQUENCE: 9
ataagaatgc ggccgcggaa gaactttgac acgtt                                35

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer pca13

<400> SEQUENCE: 10
gctctagagg aagttggata gtgctt                                          26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer pca25

<400> SEQUENCE: 11
ccatcgatgt agttccatca gatatt                                          26

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:PCR
      amplification primer pca23

<400> SEQUENCE: 12
ccgctcgagg gtaggtagta tagttaga                                        28

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:diagnostic
      PCR primer in coding region of ura4+

<400> SEQUENCE: 13
gagaaagaat gctgagtag                                                  19

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:diagnostic
      PCR primer in coding region of his3+

<400> SEQUENCE: 14
gagtctttaa ttcattac                                                   18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:diagnostic
      PCR primer in region outside of flanking fragment of dga1+

<400> SEQUENCE: 15
```
cgatagtagt caataccag                                              19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:diagnostic
      PCR primer in region outside of flanking fragment of plh1+

<400> SEQUENCE: 16
gtatattagt attgcctaat                                             20

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:RT-PCR
      primer PLH5

<400> SEQUENCE: 17
acgcgtcgac catggcgtct cccaagaag a                                 31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:RT-PCR
      primer PLH3

<400> SEQUENCE: 18
tcccccgggt taatttctag gtttatcgag                                  30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:PCR
      amplification primer DGA1-5

<400> SEQUENCE: 19
gggaattcca tatgtcagaa gaaacataa                                   29

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence:PCR
      amplification primer DGA1-3

<400> SEQUENCE: 20
tcccccgggt taggctgaca acttcaat                                    28

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:E. coli
      genomic DNA PCR amplification primer DGK5

<400> SEQUENCE: 21

-continued

```
ggaattccat atggccaata ataccactg                                           29
```

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:E. coli
      genomic DNA PCR amplification primer DGK3

<400> SEQUENCE: 22

```
tcccccgggt tatccaaaat gcgaccat                                            28
```

<210> SEQ ID NO 23
<211> LENGTH: 345
<212> TYPE: PRT
<213> ORGANISM: Schizosaccharomyces pombe
<220> FEATURE:
<223> OTHER INFORMATION: diacylglycerol O-acyltransferase (dga1; GeneDB
      Accession No. SPCC1235.15)

<400> SEQUENCE: 23

```
Met Ser Glu Glu Thr Ser Ile Pro Gly Ile Ile Ala Ser Thr Pro Pro
  1               5                  10                  15

Ile Ser Lys Asp Ser Arg Arg Asn Val Ser His Trp Leu Gln Ala Leu
             20                  25                  30

Ala Val Phe Leu His Ser Val Ser Leu Thr Leu Thr Ala Ser Trp Tyr
         35                  40                  45

Thr Val Leu Trp Ala Phe Leu Pro Phe Trp Pro Phe Leu Ile Val Tyr
     50                  55                  60

Leu Ile Trp Leu Ile Tyr Asp Asp Gly Phe Val Thr Gly Lys Asp Arg
 65                  70                  75                  80

Gln Lys Arg Trp Leu Arg Asn Ala Pro Pro Tyr Arg Trp Phe Cys His
                 85                  90                  95

Tyr Phe Pro Ile Arg Leu His Lys Thr Thr Glu Leu Asp Ser Glu Lys
            100                 105                 110

Asn Tyr Ile Phe Gly Tyr His Pro His Gly Ile Ile Ser Leu Gly Ala
        115                 120                 125

Phe Gly Gly Phe Ala Ser Glu Gly Ala Asp Phe Ser Lys Leu Phe Pro
    130                 135                 140

Gly Ile Asn Val Ser Val Leu Thr Leu Asn Ser Asn Phe Tyr Val Pro
145                 150                 155                 160

Val Tyr Arg Asp Tyr Leu Met Ala Leu Asn Ile Asn Ser Val Ser Lys
                165                 170                 175

Lys Ser Cys Val Ser Ile Leu Ser Arg Lys Pro Gly Asp Ser Val Leu
            180                 185                 190

Ile Val Ile Gly Gly Ala Gln Glu Ser Leu Leu Ser Arg Pro Gly Gln
        195                 200                 205

Asn Asn Leu Val Leu Lys Lys Arg Phe Gly Phe Val Lys Leu Ala Phe
    210                 215                 220

Leu Thr Gly Ser Ser Leu Val Pro Cys Phe Ala Phe Gly Glu Ser Asp
225                 230                 235                 240

Ile Phe Glu Gln Val Asp Asn Asn Pro Arg Thr Arg Ile Tyr Lys Phe
                245                 250                 255

Gln Glu Ile Val Lys Lys Ile Ala Gly Phe Thr Val Pro Phe Phe Tyr
            260                 265                 270

Gly Arg Gly Leu Leu Asn Lys Thr Phe Gly Leu Met Pro Trp Arg Lys
        275                 280                 285
```

```
Pro Ile Asn Ile Val Val Gly Glu Pro Ile Asp Val Pro Lys Lys Ser
    290                 295                 300

His Pro Thr Asn Gln Glu Ile Tyr Glu Val His Glu Glu Tyr Ile Arg
305                 310                 315                 320

Arg Leu Glu Gly Leu Trp Asn Lys Tyr Lys Asp Val Phe Leu Pro Asn
                325                 330                 335

Arg Ile Ser Glu Leu Lys Leu Ser Ala
            340                 345

<210> SEQ ID NO 24
<211> LENGTH: 623
<212> TYPE: PRT
<213> ORGANISM: Schizosaccharomyces pombe
<220> FEATURE:
<223> OTHER INFORMATION: phospholipid-diacylglycerol acyltransferase
      (plh1, GeneDB Accession No. SPBC776.14, Pombe LRO1 Homolog 1),
      Lecithin:cholesterol acyltransferase

<400> SEQUENCE: 24

Met Ala Ser Ser Lys Lys Ser Lys Thr His Lys Lys Lys Lys Glu Val
 1               5                  10                  15

Lys Ser Pro Ile Asp Leu Pro Asn Ser Lys Lys Pro Thr Arg Ala Leu
            20                  25                  30

Ser Glu Gln Pro Ser Ala Ser Glu Thr Gln Ser Val Ser Asn Lys Ser
        35                  40                  45

Arg Lys Ser Lys Phe Gly Lys Arg Leu Asn Phe Ile Leu Gly Ala Ile
    50                  55                  60

Leu Gly Ile Cys Gly Ala Phe Phe Phe Ala Val Gly Asp Asp Asn Ala
65                  70                  75                  80

Val Phe Asp Pro Ala Thr Leu Asp Lys Phe Gly Asn Met Leu Gly Ser
                85                  90                  95

Ser Asp Leu Phe Asp Asp Ile Lys Gly Tyr Leu Ser Tyr Asn Val Phe
            100                 105                 110

Lys Asp Ala Pro Phe Thr Thr Asp Lys Pro Ser Gln Ser Pro Ser Gly
        115                 120                 125

Asn Glu Val Gln Val Gly Leu Asp Met Tyr Asn Glu Gly Tyr Arg Ser
    130                 135                 140

Asp His Pro Val Ile Met Val Pro Gly Val Ile Ser Ser Gly Leu Glu
145                 150                 155                 160

Ser Trp Ser Phe Asn Asn Cys Ser Ile Pro Tyr Phe Arg Lys Arg Leu
                165                 170                 175

Trp Gly Ser Trp Ser Met Leu Lys Ala Met Phe Leu Asp Lys Gln Cys
            180                 185                 190

Trp Leu Glu His Leu Met Leu Asp Lys Lys Thr Gly Leu Asp Pro Lys
        195                 200                 205

Gly Ile Lys Leu Arg Ala Ala Gln Gly Phe Glu Ala Ala Asp Phe Phe
    210                 215                 220

Ile Thr Gly Tyr Trp Ile Trp Ser Lys Val Ile Glu Asn Leu Ala Ala
225                 230                 235                 240

Ile Gly Tyr Glu Pro Asn Asn Met Leu Ser Ala Ser Tyr Asp Trp Arg
                245                 250                 255

Leu Ser Tyr Ala Asn Leu Glu Glu Arg Asp Lys Tyr Phe Ser Lys Leu
            260                 265                 270

Lys Met Phe Ile Glu Tyr Ser Asn Ile Val His Lys Lys Lys Val Val
        275                 280                 285
```

-continued

```
Leu Ile Ser His Ser Met Gly Ser Gln Val Thr Tyr Tyr Phe Phe Lys
    290                 295                 300

Trp Val Glu Ala Glu Gly Tyr Gly Asn Gly Gly Pro Thr Trp Val Asn
305                 310                 315                 320

Asp His Ile Glu Ala Phe Ile Asn Ile Ser Gly Ser Leu Ile Gly Ala
                325                 330                 335

Pro Lys Thr Val Ala Ala Leu Leu Ser Gly Glu Met Lys Asp Thr Gly
                340                 345                 350

Ile Val Ile Thr Leu Asn Ile Leu Glu Lys Phe Phe Ser Arg Ser Glu
                355                 360                 365

Arg Ala Met Met Val Arg Thr Met Gly Gly Val Ser Ser Met Leu Pro
    370                 375                 380

Lys Gly Gly Asp Val Ala Pro Asp Asp Leu Asn Gln Thr Asn Phe Ser
385                 390                 395                 400

Asn Gly Ala Ile Ile Arg Tyr Arg Glu Asp Ile Asp Lys Asp His Asp
                405                 410                 415

Glu Phe Asp Ile Asp Asp Ala Leu Gln Phe Leu Lys Asn Val Thr Asp
                420                 425                 430

Asp Asp Phe Lys Val Met Leu Ala Lys Asn Tyr Ser His Gly Leu Ala
            435                 440                 445

Trp Thr Glu Lys Glu Val Leu Lys Asn Asn Glu Met Pro Ser Lys Trp
    450                 455                 460

Ile Asn Pro Leu Glu Thr Ser Leu Pro Tyr Ala Pro Asp Met Lys Ile
465                 470                 475                 480

Tyr Cys Val His Gly Val Gly Lys Pro Thr Glu Arg Gly Tyr Tyr Tyr
                485                 490                 495

Thr Asn Asn Pro Glu Gly Gln Pro Val Ile Asp Ser Ser Val Asn Asp
            500                 505                 510

Gly Thr Lys Val Glu Asn Gly Ile Val Met Asp Asp Gly Asp Gly Thr
        515                 520                 525

Leu Pro Ile Leu Ala Leu Gly Leu Val Cys Asn Lys Val Trp Gln Thr
    530                 535                 540

Lys Arg Phe Asn Pro Ala Asn Thr Ser Ile Thr Asn Tyr Glu Ile Lys
545                 550                 555                 560

His Glu Pro Ala Ala Phe Asp Leu Arg Gly Gly Pro Arg Ser Ala Glu
                565                 570                 575

His Val Asp Ile Leu Gly His Ser Glu Leu Asn Glu Ile Ile Leu Lys
            580                 585                 590

Val Ser Ser Gly His Gly Asp Ser Val Pro Asn Arg Tyr Ile Ser Asp
        595                 600                 605

Ile Gln Glu Ile Ile Asn Glu Ile Asn Leu Asp Lys Pro Arg Asn
    610                 615                 620
```

TRIACYLGLYCEROL-DEFICIENT FISSION YEAST AND ITS USES

CROSS-REFERENCE TO RELATED APPLICATION

The present invention claims priority from U.S. provisional patent application No. 60/485,385, filed on Jul. 9, 2003, which is fully incorporated herein by reference.

FIELD OF THE INVENTION

The present invention relates generally to genetically modified yeast strains, and particularly to genetically modified strains of the yeast *Schizosaccharomyces pombe*.

BACKGROUND OF THE INVENTION

Triacylglycerols (TAGs) are important energy-storage molecules which can be found in almost all eukaryotes. In mammals, TAG synthesis plays essential roles in a number of physiological processes, including intestinal fat absorption, energy storage in muscle and adipose tissue and lactation. TAG synthesis also contributes to pathological conditions such as obesity and hypertriglyceridemia (1).

TAG synthesis by the glycerol-3-phosphate pathway and the monoacylglycerol pathway is acyl-CoA dependent. The transfer of an acyl group from acyl-CoA to diacylglycerols (DAGs) catalyzed by the enzyme diacylglycerol acyl-transferase (DGAT) is regarded as the only committed reaction in TAG synthesis in the glycerolipid pathway, since DAGs are diverted from membrane glycerolipid biosynthesis (2).

Two distinct mammalian DGAT genes have been identified recently. DGAT1 was cloned based on its sequence homology to genes involved in sterol esterification (3, 4). DGAT2 was identified by its homology to a DGAT isolated from the fungus *Mortierella rammaniana* (5, 6). Other acyl-CoA dependent TAG synthesizing enzymes are likely present but are yet to be identified. In addition, acyl-CoA independent TAG synthesis was also shown to exist in eukaryotes. A DAG transacylase, which synthesizes TAG from two DAGs, was purified from rat intestinal microsomes and its activity was comparable to the activities of DGAT1 and DGAT2 (7).

In a recent study, mice lacking partial ability to synthesize TAGs were resistant to diet induced obesity, most probably due to increased energy expenditure (53).

Inhibitors of a mammalian diacylglycerol acyl-transferase gene DGAT1 and possibly other similar enzymes thus represent exciting novel drugs which might be useful to treat or prevent obesity (54). To date, few effective therapies are available for people suffering from obesity.

A further study has proven that synthesis of TAGs prevents fatty acid-induced lipotoxicity in mammalian cells (12). Lipotoxicity refers to the toxic effect that circulating excess fatty acids (for example in the form of diacylglycerols) have on certain non-adipose cells and tissues, particularly liver, muscle, and pancreatic beta cells, and is often seen in Type II diabetes patients (55). The effects of lipotoxicity depend on the particular cell type, and include induction of insulin resistance, for example in smooth muscle cells, and cell death (termed lipoapoptosis), for example in beta cells.

Overload of TAGs and fatty acids in non-adipose tissues, e.g. pancreas, heart, muscle, could damage those tissues by a inducing lipoapoptosis. Death of pancreatic beta cells is key to the pathogenesis of type II diabetes while death of cardiomyocytes could lead to heart failure. To date, our understanding of the molecular mechanisms underlying lipoapoptosis is limited and no therapy exists to prevent or slow down lipoapoptosis.

There is no simple yet powerful model system for developing anti-lipoapoptosis therapies to treat Type R diabetes and cardiomyopathy. A TAG-deficient budding yeast strain and a knock-out mouse strain with reduced TAG in certain tissues exist but neither showed any phenotypic relevance to lipoapoptosis.

SUMMARY OF THE INVENTION

In one aspect, the present invention provides a fission yeast strain comprising non-functional dga1 and plh1 genes. In one embodiment, the yeast strain is *Schizosaccharomyces pombe* Δplh1 Δdga1 double deletion mutant.

In another aspect, the invention provides a method of making a fission yeast strain having non-functional dga1 and plh1 genes, comprising functionally interrupting the dga1 and plh1 genes in a fission yeast strain.

The yeast of the present invention is susceptible to lipotoxicity including lipoapoptosis. Therefore, the yeast strains of the invention may be used to study the processes and molecules involved in lipoapoptosis or lipotoxicity. TAG-deficient fission yeast represents the first unicellular model system that is suitable for the study of lipoapoptosis and lipotoxicity. Lipoapoptosis appears to be critical to the development of type II diabetes and cardiomyopathy. The yeast strains according to the invention may therefore be used to screen for compounds that inhibit lipoapoptosis and lipotoxicity and that may be therapeutically useful in disorders associated with lipoapoptosis or lipotoxicity, including but not limited to, type BI diabetes and cardiomyopathy. The yeast strains may be advantageously used in high throughput screening of compounds.

Thus, in another aspect, the present invention provides a method of screening or identifying a compound that inhibits or prevents lipotoxicity, comprising treating with a compound a culture of a fission yeast strain comprising non-functional dga1 and plh1 genes; exposing the treated culture to conditions that are suitable for inducing lipotoxicity in an untreated culture; and detecting lipotoxicity in the treated culture. In one embodiment, lipotoxicity is lipoapoptosis.

The compounds identified by this method may include compounds that inhibit or prevent lipoapoptosis in pancreatic beta cells and cardiomyocytes, including compounds effective in the treatment or prevention of disorders associated with lipoapoptosis such as diabetes, coronary heart disease, heart failure and cardiomyopathy. Such compounds may include small molecules and bioactive agents such as proteins, peptides, antibodies, hormones, lipids and nucleic acids.

In one embodiment, the method comprises the steps of growing a culture of fission yeast according to the invention, such as *Schizosaccharomyces pombe* Δplh1 Δdga1 double deletion mutant, treating the culture with a compound, exposing the treated culture to conditions that are suitable for inducing lipoapoptosis in an untreated culture and detecting whether the treated culture has undergone lipoapoptosis.

The yeast strains according to the invention can also be used to study TAG synthesis and to identify inhibitors of TAG synthesis and which inhibitors may be effective in treating or preventing disorders, such as obesity. Thus, in another aspect, the present invention provides a method for screening or identifying a compound that inhibits or prevents TAG synthesis, comprising treating with a compound a culture of a fission yeast strain comprising non-functional dga1 and plh1 genes, wherein the yeast strain comprises an exogenous gene which is expressible in the yeast strain and which, when expressed in the yeast strain, results in TAG synthesis; and detecting any TAG synthesis in the culture. In certain embodiments, TAG synthesis may be indirectly deleted by measuring cell viability. The compounds identified by this method may include compounds effective in the treatment of obesity, diabetes, coronary heart disease, heart failure or cardiomyopathy.

In one embodiment, the inhibitors of TAG synthesis may be identified by transforming TAG-deficient fission yeast such as *Schizosaccharomyces pombe* Δplh1 Δdga1 double deletion mutant with a mammalian gene encoding a protein involved in TAG synthesis, such as human DGAT, growing transformed yeast cell in culture, treating the culture with a compound and detecting if any TAG is synthesized by the transformed yeast cell.

The terms "inhibits" or "prevents" or "inhibiting" or "preventing" refer to reducing, lessening, blocking completely or partially, a particular cellular function, and include functionally disrupting a cellular function such that the end-product of that cellular function, or the phenotype associated with that cellular function is reduced or eliminated as compared to a control where the cellular function is not inhibited or prevented.

In another aspect the invention therefore provides a method of screening or identifying a gene that complements non-functional dga1 and plh1 genes, comprising transforming a fission yeast strain comprising non-functional dga1 and plh1 genes with an exogenous gene; culturing the transformed yeast strain; and detecting any TAG synthesis in the culture. The exogenous gene may be any gene from another species, including mammals, that is suspected to be involved in TAG synthesis.

The term "complements" refers to genetic complementation of a particular yeast strain by expression of an exogenous gene within that yeast strain such that the phenotype associated with the yeast strain genotype is altered or corrected to correspond to wildtype phenotype, under some or all conditions.

Kits or commercial packages comprising the yeast strain of the present invention and instructions for screening or identifying a compound that inhibits or prevents TAG synthesis, or for screening or identifying a compound that inhibits or prevents lipotoxicity including lipoapoptosis, or for screening or identifying a gene that complements the non-functional dga1 and plh1 genes, are also provided.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
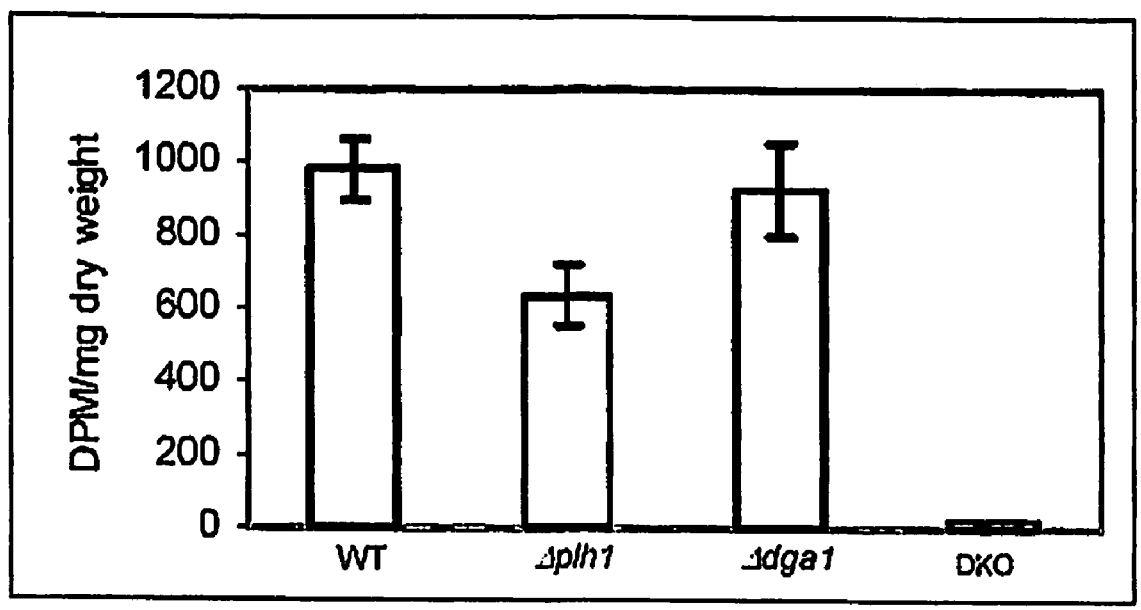
FIG. 1 is a graphical representation of results obtained from [$^3$H] oleate pulse labeling of wildtype (WT), single deletion strains Δplh1 and Δdga1, and double deletion strain Δplh1 Δdga1(DKO)

Four genes, i.e. DGA1, LRO1, ARE1 and/or ARE2, have been found to encode proteins capable of synthesizing TAG in the budding yeast *Saccharomyces cerevisiae* (*S. cerevisiae*) (8, 9, 10, 11). Dga1p (i.e. Dga1 protein) is highly homologous to mammalian DGAT2 while LRO1 encodes the Lro1p protein which has significant sequence similarity to the mammalian enzyme lecithin cholesterol acyltransferase (LCAT). Dga1p utilizes acyl-CoA to esterify DAG while Lro1p transfers an acyl group from a phospholipid molecule to the sn-3 position of DAG. Dga1p and Lro1p mediate the bulk of TAG synthesis; however, in their absence, 2-4% of normal TAG synthesis could still be detected.

The fission yeast *Schizosaccharomyces pombe* (*S. pombe*), similar to the budding yeast, is genetically tractable and equipped with a rich repertoire of molecular tools and a completely sequenced genome (13, 14). Although the fission and budding yeasts are as divergent from each other as each from mammals, S. pombe has been shown to have greater similarity to mammals at least in certain steps of cell division and in aspects of stress signalling (15). The enzymes and pathways of lipid metabolism, their physiological significance, and their resemblance to mammalian systems are largely unexplored in *S. pombe*.

To identify potential *S. pombe* genes that may be involved in TAG synthesis, the fission yeast genome database was searched for homologous sequences to human DGAT1 (hDGAT1), human DGAT2 (bDGAT2) and the budding yeast LRO1 gene using tBLASTX.

A sequence with significant homology to hDGAT2 (40 percent identity at protein level) was identified and named dga1+ (GeneDB systematic name: SPCC1235.15 (SEQ ID NO:23)). dga1+ encodes a 345-residue protein with at least one transmembrane domain. The region of the putative glycerol phospholipid domain in hDGAT2 was also found to be conserved in Dga1p (45% percent identity over 80 amino acids).

In addition, as previously reported, an open reading frame highly homologous (45 percent identity at protein level) to the budding yeast LRO1 was found in the fission yeast genome and named plh1+ (for Pombe LRO1 Homolog 1, GeneDB systematic name: SPBC776.14 (SEQ ID NO:24)).plh1+ predicts a protein of 623 amino acids, with a putative transmembrane domain near its N terminus. Plh1p also has a conserved serine lipase motif HS(M/L)G between amino acids 292-296.

These genes have been interrupted in the yeast strain of the present invention so as to provide a yeast strain that is unable to synthesize TAGs. Similar to their *S. cerevisiae* counterparts, Dga1p in *S. pombe* has DGAT activity while *S. pombe* Plh1p is a PDAT. One important difference is that unlike *S. cerevisiae,* whereas a small but significant amount of TAG can be detected in LRO1 and DGA1 double deletion cells, no significant TAG synthesis was observed when both plh1+ and dga1+ were deleted. In agreement with Oelckers et al. (10), the results presented herein indicate that Plh1p or the PDAT activity is responsible for the majority of TAG synthesis when yeast cells are undergoing exponential growth.

Thus, the present invention relates to a fission yeast strain comprising non-functional dga1+ and plh1+ genes. As a result, the yeast strain is rendered TAG-deficient.

The fission yeast may be any fission yeast strain of the genus *Schizosaccharomyces*, including strains of the species *S. pombe, S. japonicus* and *S. octosporus*. In one embodiment, the fission yeast strain belongs to the species *S. pombe.*

The dga1+ gene and the plh1+ gene refer to the *S. pombe* genes that have the sequences identified as GeneDB Accession No. SPCC1235.15 (SEQ ID NO:23) and GeneDB Accession No.SPBC776.14 (SEQ ID NO:24), respectively, or where the yeast strain is other than *S. pombe,* the homologous genes in such other fission yeast strain. The term "homologous" refers to a nucleotide sequence that differs from a reference sequence (here *S. pombe* genes dga1 or plh1) only by one or more conservative substitutions, or by one or more non-conservative substitutions, deletions, or insertions located at positions of the sequence that do not affect the biological function of the translated protein when expressed.

Preferably, a homologous sequence is one that is at least 45%, more preferably 50%, 55%, 60%, 65%, 70%, 75%, 80%, and even more preferably 85%, 87%, 90%, 93%, 96% and most preferably 99% identical when optimally aligned at the nucleotide level to the dga1 or plh1 *S. pombe* gene sequence, using for example, the Align Program (Myers and Miller, CABIOS, 1989, 4:11-17) or FASTA. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine, or as described herein). Examples of useful software include the programs Pile-up and PrettyBox. Such software matches similar sequences by assigning degrees of homology to various substitutions, deletions, insertions, and other modifications. Nucleotide sequences are aligned to maximize identity. Gaps may be artificially introduced into the sequence to attain proper alignment. Once the optimal alignment has been set up, the degree of homology is established by recording all of the positions in which the nucleotides, or amino acids of the translated polypeptide, of both sequences are identical or homologously conserved, relative to the total number of positions.

A skilled person will be able to readily identify homologous genes in other fission yeast strains other than *S. pombe* using known methods. For example, where the genome of the species has been sequenced, the genome can be searched for homologous gene sequences, the gene cloned, and the activity of the resulting expressed protein tested to confirm that the gene is a functional homologue to the dga1 or plh1 gene of *S. pombe*.

The term "TAG-deficient" is used to describe a lack of detectable TAG synthesis that may result, for example from defective TAG synthesizing enzymes expressed at normal levels or a low or lack of expression of functional TAG synthesizing enzymes. TAG is not detectable when no significant levels of TAG, as compared to the wildtype yeast strain, can be detected using standard methods of detecting cellular TAG levels, for example, such as those described herein, as will be understood by a skilled person. The yeast strain has non-functional dga1 and plh1 genes, meaning that these genes have been functionally interrupted to result in no or low expression of Dga1p and Plh1p, or expression of defective variants of Dga1p and Plh1p. Functional interruption refers to modification of the coding sequence or a control sequence, for example a promoter sequence or transcriptional control element, of the relevant genes such that no functional gene product is produced, or is produced at low levels, or a non-functional gene product is produced. Functional interruption includes insertion, deletion or substitution of one or more nucleotides within the coding or transcriptional control elements of the relevant genes. For example, the coding region, or a substantial portion thereof, may be replaced with a coding region for a selectable marker.

The TAG-deficient yeast strain of the present invention may be constructed using standard yeast cloning methods known in the art and the invention provides a method of making a *Schizosaccharomyces* yeast strain having non-functional dga1 and plh1 genes, comprising functionally interrupting the dga1 and plh1 genes in a *Schizosaccharomyces* yeast strain. For example, the dga1+ and plh1+ genes may be interrupted by insertion of a marker gene into the coding region of the genes using homologous recombination methods, such as those described herein and as will be understood by a skilled person. Briefly, the regions flanking the gene or sequence that is to be interrupted may be amplified and cloned into a yeast vector containing a suitable selectable marker gene (for example ura4+) so as to create a gene replacement cassette. The wildtype yeast strain from which the TAG-deficient strain is to be generated is then transformed with the gene replacement cassette vector, and transformants expressing the marker gene are selected, indicating that such transformants have undergone homologous recombination so as to replace the target gene (here dga1 or plh1) with the marker gene.

In one embodiment, the TAG-deficient fission yeast strain is *Schizosaccharomyces pombe* Δdga1 Δplh1 double deletion mutant. In a particular embodiment, the double deletion strain is generated by replacing the dga1 and plh1 coding sequences with a selectable marker, the *S. pombe* ura4+ or his3+ coding region respectively, as set out in the Examples below.

Deletion of the dga1+ and plh1+ genes resulted in a fission yeast strain that does not synthesize TAGs. The level of triacylglycerol synthesis can be determined using standard methods known in the art. For example, TAG levels can be determined by extraction of total cellular lipids and visualization by thin layer chromatography separation and iodine vapour staining. TAG synthesis can be quantified using labelled substrates, for example a radiolabelled fatty acid, and performing extraction and separation of lipids and measuring the incorporation of the labelled fatty acid into the TAG mass extracted from the cells, in comparison to levels of incorporation in wildtype.

The TAG-deficient yeast strain generally is not heat or cold sensitive, and is viable at a range of temperature (16° C., 30° C. and 37° C.) with no observable abnormal growth morphologies.

However, *S. pombe* cells without detectable TAG undergo apoptosis upon entry into stationary phase, as measured by cell viability assays, for example, colony forming unit assays, or by visualization of nuclear DNA, for example by fluorescent staining of the DNA, to monitor DNA fragmentation upon entry into stationary phase.

The present TAG-deficient yeast strain can also be induced to undergo apoptosis in response to exposure to diacylglycerols and fatty acids, likely due to an accumulation of diacylglycerols in early stationary phase.

Apoptosis is a form of cell death that plays a critical role in the development and homeostasis of all multicellular organisms. Recent studies have proven that apoptosis also exists in unicellular organisms, such as the yeast *S. cerevisiae* (33). Various stimuli can cause apoptotic cell death in *S. cerevisiae*, including oxygen radicals, sexual pheromone, UV, salt stress and expression of proapoptotic mammalian genes, e.g. Bax (reviewed in 33). Mutations in certain *S. cerevisiae* genes could also trigger apoptosis (31; 39). All cases of apoptosis documented so far in *S. cerevisiae* were shown to be associated with increased production of reactive oxygen species ("ROS"), which is believed to be a key regulator for apoptosis in both uni- and multi-cellular organisms. Apoptosis in *S. pombe* is much less well characterized and the only reported cases were induced by overexpression of mammalian Bak (40) or *C. elegans* Ced-4 (41). The cells of the present TAG-deficient *S. pombe* strain lost viability upon entry into stationary phase and displayed prominent apoptotic markers, which were not observed when cells were killed by treatment of C2 ceramide or sphingoid bases, as described in the Examples below.

Since the yeast strain of the present invention is TAG-deficient, it provides a useful system for studying TAG synthesis, for example, to identify genes homologous to dga1 and plh1. The invention therefore provides a method of screening or identifying a gene that complements dga1 and plh1 genes, comprising transforming a fission yeast strain comprising non-functional dga1 and plh1 genes with an exogenous gene; culturing the transformed yeast strain; and detecting any TAG synthesis in the culture. The exogenous gene may be any gene from another species that is suspected to be involved in TAG synthesis.

The yeast strain can also be used to study the mechanism of mammalian DGAT, and to identify inhibitors of mammalian DGAT. To develop and analyze such inhibitors of mammalian DGAT, a system will be needed to produce, maintain and analyze the enzyme. The ideal system should have zero or extremely low endogenous activity and should be easy to manipulate at molecular level. The yeast strain of the invention can produce and harbour the mammalian enzyme, whose DGAT activity can then be easily assayed. Thus, the present yeast strain may be used to identify genes and to study the structure and function of gene products involved in TAG synthesis, including mammalian DGATs, and to identify the active sites of these proteins.

Identification of compounds that are effective in inhibiting one or more TAG synthesizing enzymes or which reduce or down regulate the level of one or more such enzymes, may be useful in treatment of disorders such as obesity. Thus, the yeast of the present invention can be used to identify or screen compounds effective in inhibiting gene products involved in TAG synthesis, including mammalian DGAT, and which may therefore be effective in treating or preventing obesity, type II diabetes, coronary heart disease, heart failure and other disorders that can be treated or prevented by controlling the level of TAG synthesis.

Thus, the present invention provides a method for screening or identifying compounds that inhibit TAG synthesis, including compounds effective in the treatment of obesity, type II diabetes, coronary heart disease and heart failure.

In one embodiment, the inhibitors of TAG synthesis may be identified by transforming a TAG-deficient fission yeast cell such as Schizosaccharomyces pombe Δplh1 Δdga1 double deletion mutant with an exogenous gene which is expressible in the fission yeast cell, and which, when expressed in the double deletion mutant, results in TAG synthesis, growing the transformed yeast cell in culture, treating the culture with a compound and detecting if any TAG is synthesized by the transformed yeast cell.

Fission yeast is extremely easy to manipulate at molecular level when compared with most other experimental systems. Thus, as will be known to a skilled person, the yeast strain comprising an exogenous gene may be readily prepared, for example by transforming with a plasmid expressing, at low or high levels, the exogenous gene in the TAG-deficient fission yeast.

The gene may be any gene involved in TAG synthesis that when expressed in the fission yeast strain comprising non-functional dga1+ and plh1+ genes is able to synthesize TAG. For example, the gene may be a mammalian, particularly human, diacylglycerol acyl-transferase (GAT) or phospholipid diacylglycerol acyl-transferase (PDAT) homologue such as lethicin cholesterol acyltransferase (LCAT), or the gene for enzymes such as an acyl-CoA cholesterol acyl transferase (ACAT) or a monoacylglycerol acyl transferase (MGAT).

The plasmid may be any fission yeast expression plasmid, for example pRep1 or pRep41, and will typically include the gene of interest that is to be expressed, under control of a promoter that can be recognized by S. pombe transcription machinery. The promoter may be constitutive or inducible, and may be a strong or weak promoter, resulting in high or low levels of expression of the gene of interest. The plasmid may further include a selectable marker, for example a gene expressing an auxotrophic selection gene supplying a nutritional requirement of the host yeast strain, such as the leu2 gene, the ura4 gene or the his3 gene, or a dominant selection gene such as a gene for resistance to an antibiotic such as G418, phleomycin or hygromycin B, or a reporter gene for example the β-gal gene.

Culturing or growing the transformed yeast cell in culture will be performed using standard techniques known in the art. A skilled person will understand how to determine the appropriate growth medium to use, and whether to include or exclude as necessary any components required for selection of the selectable marker, and which temperature and growth conditions to use. Generally, S. pombe will be grown at 30° C., in well-aerated medium if in liquid culture.

The culture may be treated with any compound that is to be tested for its ability to inhibit TAG synthesis. For example, the compound may be a small molecule or a bioactive agent such as a protein, peptide, antibody, hormone, lipid or nucleic acid. Typically, the compound will be added to the growth medium, for example to a liquid culture at early log phase.

Synthesis of TAG may be detected using known techniques. For example, as mentioned above, total cellular lipids may be extracted, the TAGs separated from other lipids, for example by thin layer chromatography, and visualized. As well, once extracted, the total cellular lipids may be analysed using mass spectrometry techniques as would be known in the art. Addition of a labelled substrate of TAG synthesis, such as a labelled fatty acid, may assist in visualization of any TAG that is synthesized. For example, the substrate may be labelled with a radioactive molecule, a chemiluminescent molecule, a fluorescent molecule, an enzyme that cleaves a reagent to produce a coloured molecule, a coloured molecule or a heavy metal complex.

TAG synthesis may also be detected indirectly by exposing the culture to conditions that are suitable for inducing lipoapoptosis in a culture not expressing the exogenous gene and detecting lipoapoptosis in the exposed culture, as described below.

The fact that the S. pombe Δdga1 Δplh1 cells lost viability upon entry into stationary phase is both intriguing and informative. Normal yeast cells including S. pombe cells arrest cell growth and enter a resting state called stationary phase upon nutritional limitation (44). It is known that yeast cells accumulate neutral lipids after diauxic shift, possibly as a result of phospholipids remodeling. Although TAG might be required for yeast cells to survive stationary phase, possibly as an energy source, it is more likely that TAG serves as an inert storage depot for such bioactive molecules as DAG and fatty acids. Failure to convert DAG and fatty acids into TAG could result in deleterious consequences. In fact, Schaffer and colleagues have recently reported that accumulation of triglycerides protects against fatty acid induced lipotoxicity in mammalian cells (12). In addition, a mutation in Drosophila DGAT gene led to apoptotic cell death of egg chamber cells, although the exact mechanism was unclear (29). In the results presented herein, several lines of evidence support a role of DAG in the death of S. pombe Δdga1 Δplh1 cells: first, mutant cells grown in rich media accumulate DAG upon entry into stationary phase; second, exogenous 1,2-dioctanoyl-sn-glycerol ("diC8 DAG") causes exponentially growing mutant cells to undergo apoptosis; third, addition of palmitate and oleate induce DAG synthesis and trigger apoptosis, which could be largely rescued by overexpression of a bacterial DAG kinase; fourth, dihydrosphingosine (DHS), phytosphingosine (PHS) or ceramide kill mutant cells in a manner other than apoptosis.

The results presented herein indicate that S. pombe bears resemblance to the situation in higher eukaryotes, as recent data suggested that TAG synthesis could be an essential process for higher cells. Free fatty acids play a key role in the pathogenesis of type II diabetes and many studies suggested that high level of plasma free fatty acids and excessive accumulation of fatty acids in non-adipose tissues causes insulin resistance and cell death, especially apoptosis of the pancreatic beta cells (50, 51). Using Zucker diabetic fatty fa/fa (ZDF) rats, Unger and colleagues showed convincingly that fatty acids and over-accumulation of TAG caused pancreatic beta cells to undergo lipoapoptosis, which was probably mediated by increased production of ceramide and nitric oxide (NO) (reviewed in 51). Studies by Schaffer and colleagues showed that ROS, rather than ceramide, was critical in the fatty acids-induced apoptosis of CHO cells (38). The involvement of DAG and protein kinase C (PKC) in palmitate-induced generation of ROS was demonstrated when cultured aortic smooth muscle cells were incubated with high level of palmitate (52).

The fission yeast strains such as S. pombe mutant cells deficient in TAG synthesis may therefore serve as an excellent model system to study the molecular mechanisms of lipotoxicity and lipoapoptosis, since the effect of fatty acids on cell growth are more pronounced and can be easily detected in these mutants. As well, these TAG-less strains could offer a novel platform to screen for compounds that might prevent fatty acids-induced lipoapoptosis by blocking the apoptotic response to high levels of fatty acids or DAGs, including compounds which may be effective in the treatment or prevention of disorders associated with lipotoxicity and lipoapoptosis, including type II diabetes and cardiomyopathy.

The present invention therefore provides a method of screening or identifying compounds that inhibit or prevent lipotoxicity, for example lipoapoptosis. In one embodiment, a culture of a *Schizosaccharomyces pombe* yeast strain comprising non-functional dga1+ and plh1+ genes is treated with a compound and the treated culture is exposed to conditions that are suitable for inducing lipoapoptosis in an untreated culture and lipoapoptosis detected. The yeast is cultured in accordance with known techniques, and the culture may be treated with any compound that is to be tested for its ability to inhibit or prevent lipoapoptosis by addition of the test compound to the growth medium before the culture enters stationary phase, for example during log phase, or at the start of stationary phase. The compound may be a small molecule or a bioactive agent such as a protein, peptide, antibody, hormone, lipid or nucleic acid.

Conditions that induce lipoapoptosis in an untreated culture in an *S. pombe* strain having non-functional dga1 and plh1 genes include exposure of the culture to diacylglycerols or fatty acids. In one embodiment, fatty acids such as oleic acid or palmitic acid, are added at a final concentration in the growth medium of about 0.5 mM to about 1 mM of fatty acid at early log phase. In another embodiment, a diacylglycerol such as diC8 diacylglycerol, is added at a concentration of about 0.1 to about 0.3 mM. The fatty acids or DAG may be dissolved in a solubilizing agent, for example a stock of fatty acid in chloroform maybe dissolved in a 1:1 mixture of tyloxapol and ethanol prior to addition to the growth medium, or the DAG may be dissolved in DMSO.

Detecting whether the *S. pombe* cells undergo lipoapoptosis may be performed by examining the cells for viability and for production of apoptotic markers. Cell viability may be measured using standard methods, including colony forming assays or by staining for dead cells using, for example propidium iodide. Apoptotic markers include fragmented nuclear DNA, which maybe visualized by DAPI fluorescent staining or by labelling of free 3' OH termini with fluorescently tagged nucleotides, for example by a TUNEL assay. Another apoptotic marker is the exposed phosphatidylserine at the outer leaflet of the plasma membrane, which may be visualized by staining with fluorescently labelled annexin V, which is a 35-36 kDa, Ca 2+-dependent, phospholipid binding protein with a high affinity for phosphatidylserine. Production of reactive oxygen species such as superoxide ($O2^-$) and hydrogen peroxide ($H_2O_2$) is another marker for apoptosis, and may be identified by treating cells with fluorescent molecule precursors that fluoresce upon oxidation, for example dihydroethidium, which is oxidized to ethidium by reactive oxygen species. Apoptotic markers may therefore be detected by adding a detection molecule which, as used herein, refers to any labelled molecule that permits detection of apoptotic markers, for example by binding to the apoptotic marker or which is a precursor that becomes detectable in the presence of an apoptotic marker.

Compounds identified by the methods of the present invention may be useful in treating or preventing obesity or in treating or preventing type II diabetes and cardiomyopathy and the invention therefore extends to such compounds.

Kits or commercial packages comprising the yeast strain of the present invention and instructions for screening or identifying a compound that inhibits or prevents TAG synthesis, or for screening or identifying a compound that inhibits or prevents lipotoxicity including lipoapoptosis, or for screening or identifying a gene that complements the yeast strain of the invention, are also provided.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

The word "comprising" is used as an open-ended term, substantially equivalent to the phrase "including, but not limited to". The following examples are illustrative of various aspects of the invention, and do not limit the broad aspects of the invention as disclosed herein.

EXAMPLES

TAGs are important energy storage molecules for nearly all eukaryotic organisms. In this study, we found that two gene products (Plh1p and Dga1p) are responsible for the terminal step of TAG synthesis in the fission yeast *Schizosaccharomyces pombe* through two different mechanisms: Plh1p is a phospholipid diacylglycerol acyltransferase (PDAT) while Dga1p is an acyl-CoA: diacylglycerol acyltransferase (DGAT). Cells with both dga1+ and plh1+ deleted (DKO cells) lost viability upon entry into stationary phase and demonstrated prominent apoptotic markers. Exponentially growing DKO cells also underwent dramatic apoptosis when briefly treated with diacylglycerols (DAG) or free fatty acids. We provide strong evidence suggesting that DAG, not sphingolipids, mediates fatty acids-induced lipoapoptosis in yeast. Lastly, we show that generation of reactive oxygen species (ROS) is essential to lipoapoptosis.

Materials and Methods

Yeast strains, general techniques and reagents: *Schizosaccharomyces pombe* strains MBY257 (h-, his3-D1, ade6-M210, leu1-32, ura4-D18) and MBY266 (h+, his3-D1, ade6-M210, leu1-32, ura4-D18) were used in this study (16). Growth media (YES and EMM) and basic genetic, cell and biochemical techniques were used according to a previous report (17). Transformation of yeast was performed with electroporation, followed by prototrophic selection (18). Yeast extract, Yeast Nitrogen Base, Bacto-peptone and Bacto-agar were from Difco Laboratories; D-dextrose, D-galactose and D-raffinose were from Sigma. 3,3,5,5-Tetramethyl-1-1-pyrroline-n-oxide, 1,2-dioctanoyl-sn-glycerol, oleic acid, palmitic acid, 4',6-diamidino-2-phenylindole (DAPI) and Nile Red were from Sigma. N-acetylsphigosine (C2-Ceramide) was from US Biological. [1-$^{14}$C] oleoyl-CoA, 1-Stearoyl-2-[$^{14}$C] arachidonylsn-glycerol, 1-palmitoyl-2 [1-$^{14}$C] oleoyl phosphatidylethanolamines (PE) and [9,10(n)-$^3$H] oleic acid were from Amersham Biosciences. In situ cell death detection kit and Annexin-v-fluos were from Roche Applied Science.

Disruption of plh1+, dga1+ and pca1+: For plh1+ gene disruption, the entire coding region of plh1+ was replaced by the *S. pombe* his3+ gene. Two pairs of primers: PLH1-55 (GGGGTACCACACCCTATTTGCAACA) [SEQ ID NO.:1] and PLH1-53 (CCGCTCGAGGAATTGCTTGAGCAG-CAAC) [SEQ ID NO.:2]; PLH1-35 (CGGGATCCCGA-CAAACGAATATGATAAA) [SEQ ID NO.:3] and PLH1-33

(GCTCTAGAGGCTCCATAGAAGGTGAAG) [SEQ ID NO.:4] were used to amplify DNA fragments flanking the coding region of plh1+. The PCR products were cloned into a vector containing the his3+ gene to create a gene replacement cassette.

For dga1+ gene disruption, the entire coding region was replaced by the *S. pombe* ura4+ gene. Two pairs of primers: DGA1-55 (GGGGTACCGAATCCATGGGTAGTGAT) [SEQ ID NO.:5] and DG11-53 (CCGCTCGAGCCCGTTC-TATATAATCGT) [SEQ ID NO.:6]; DGA1-35 (CGGGATC-CCTTATTGGCCTATGCAATA) [SEQ ID NO.:7] and DGA1-33 (GCTCTAGACTGAATGAATATTAGTAACGC) [SEQ ID NO.:8] were designed and a gene replacement cassette containing the ura4+ gene was constructed to disrupt dga1+.

For pca1+ gene disruption, the entire coding region was replaced by the $kan^R$ marker (19). Two pairs of primers: pca15 (ATAAGAATGCGGCCGCGGAA-GAACTTTGACACGTT) [SEQ ID NO.:9] and pca13 (GCTCTAGAGGAAGTTGGATAGTGCTT) [SEQ ID NO.: 10]; pca25 (CCATCGATGTAGTTCCATCAGATATT) [SEQ ID NO.:11] and pca23 (CCGCTCGAGGGTAGGTAGTAT-AGTTAGA) [SEQ ID NO.:12] were used to amplify DNA fragments flanking the coding region of pca1+.

The PCR products were cloned into pFA6akanMX4 (19), flanking $kan^R$.

Transformation of yeast:. About 2 micrograms of gene replacement cassettes were used to transform wild type strains MBY266 and MBY257 by electroporation. Transformed cells were suspended in 200 μl 1.2M sorbitol and selected on EMM plates with appropriate amino acid supplements. Clones bearing the individual or double gene deletions were identified by diagnostic PCR with primers in the coding region of ura4+ or his3+ (GAGAAAGAATGCTGAGTAG [SEQ ID NO.:13] for ura4+; and GAGTCTTTAATTCAT-TAC [SEQ ID NO.:14] for his3+), and primers in the region outside of the flanking fragment of dga1+ or plh1+ (CGAT-AGTAGTCAATACCAG [SEQ ID NO.:15] and GTATATT-AGTATTGCCTAAT [SEQ ID NO.:16] accordingly). The DKO strain was constructed by consecutive deletions of plh1+ and dga1+ in MBY266. The TKO strain was generated by deletion of pca1+ from the DKO strain.

Expression plasmids construction: The entire open reading frame of plh1+ was generated by RT-PCR using primers PLH5 (ACGCGTCGACCATGGCGT CTTCCCAA-GAAGA) [SEQ ID NO.:17] and PIH3 (TCCCCCGGGT-TAATTTCTAGGTTTATCGAG) [SEQ ID NO.:18] while the entire coding region of dga1+ was amplified by PCR using the primers DGA1-5 (GGGAATTCCATATGTCAGAAGAAA-CATAA) [SEQ ID NO.:19] and DGA1-3 (TCCCCCGGGT-TAGGCTGACAACTTCAAT) [SEQ ID NO.:20]. The products were digested by SmaI and SalI and cloned into pREP41 or pREP42GFP, downstream of an nmt1 promoter (20, 21). The open reading frame of DAG kinase was amplified from *E. coli* genomic DNA by PCR using the primers DGK5 (GGAATTCCATATGGCCAATAATACCACTG) [SEQ ID NO.:21] and DGK3 (TCCCCCGGGTTATCCAAAATGC-GACCAT) [SEQ ID NO.:22] (22). The fragment was subcloned into the SmaI and NdeI sites of pREP41.

Cell viability assay: For cell viability at different growth phases, cells were grown to various densities in YES (determined by $OD_{595}$). The number of viable cells was obtained after cells were diluted properly in distilled water and plated in triplicates on YES agar. Colonies were scored after 3 days of incubation at 30° C. For cell viability after various treatments, cells were grown to early log phase ($OD_{595}$=0.1)

before lipids or other chemicals were added. After treatment, cells were collected and viability was analyzed as described above.

DAG, fatty acid and ceramide treatment: For fatty acid treatment, palmitic acid and oleic acid were dissolved in chloroform as 500 mM stock. Each microliter of fatty acids was dissolved in 12.5 μl tyloxapol-enthanol (1:1) and added into growth medium. Wild type and DKO strains were grown to early log phase and then incubated in medium containing different concentrations (0.5 mM, 0.8 mM and 1 mM) of palmitic acid or oleic acid for 0-3 hours. Control groups were cultured in the medium added with the same volume of tyloxapol-enthanol without fatty acids. After incubation, cells were analyzed for viability and DNA fragmentation. DiC8 DAG and ceramide were dissolved in DMSO. The working concentrations for DAG was 0.1 mM, 0.2 mM or 0.3 mM, while for ceramide was 10 μM or 20 μM (23, 24).

Nile Red staining: Cells were grown to early stationary phase, washed with deionized $H_2O$ two times and incubated with 1 μg/ml of Nile Red (1 mg/ml in acetone stock). Fluorescent images were obtained with a Leica DMLB microscope (25).

Detection of apoptotic markers: All assays in this section were performed as previously described (26).

4',6-diamidino-2-phenylindole (DAPI) staining: Cells were fixed with 3.7% formaldehyde for 10 minutes, washed once with PBS containing 4% NP40 and twice with PBS, and then stained with DAPI. Cells were viewed using a Leica DMLB microscope.

Terminal deoxynucleotidyl transferase(TdT)-mediated dUTP nick-end labeling (TUNEL): Cells were fixed with 3.7% formaldehyde for 1 hr, digested with zymolase, washed with PBS, incubated in a permeabilization solution (0.1% Triton in 0.1% sodium citrate) for 2 minutes on ice, washed twice with PBS and incubated with 50 μl TUNEL mixtures for 1 hour at 37° C. Cells were washed with PBS twice and were viewed using a Leica DMLB microscope.

Annexin V staining: Cells were washed in sorbitol buffer (1.2M sorbitol, 0.5 mM $MgCl_2$, potassium phosphate, pH 6.8), digested with zymolase for 2 hrs at room temperature, harvested, washed in binding buffer (10 mM HEPES/NaOH, 140 mM NaCl, 2.5mM $CaCl_2$, 1.2 M sorbitol), pelleted and resuspended in binding buffer. 2 μl annexin-FITC and 2 μl propidium iodide were added to 38 μl cell suspension, and then incubated for 20 minutes at room temperature. The cells were harvested, suspended in binding buffer, and applied to microscopic slides.

Production of reactive oxygen species: ROS were detected by dihydroethidium (Sigma), which was used at 5 μg per ml cell culture. After incubation for 10 minutes, cells were viewed under a Leica DMLB microscope through a Texas Red filter. The free radical spin trap reagent 3,3,5,5,-tetramethyl-pyrroline N-oxide (TMPO) was used at 125 μg per ml cell culture. Cells were pretreated with TIPO for 2 hours before lipids were added.

In vivo assay of oleate incorporation: The incorporation of [$^3$H] oleate into TAG was used as a measurement of DAG esterification essentially as described (9). Briefly, cells were cultured in YES or EMM without appropriate nutrients for plasmid maintenance when necessary. Approximately 5 ml cells at logarithmic (log) phase ($OD_{595}$=0.55-0.80) were pulsed with 5 μCi of [$^3$H]oleate at 30° C. for 30 minutes with shaking. Cells were washed twice with 0.5% tergitol, once with $dH_2O$, and lyophilized. The dried cell pellets were resuspended in 50 μl of lyticase stock solution (1700 units/ml in 10% glycerol, 0.02% sodium azide) and incubated at −70° C. for one hour and at 30° C. for 15 minutes. Lipids were extracted by hexane and analyzed by Thin Layer Chromatography (TLC). The plates were developed in hexane:diethyl ether:acetic acid (70:30:1) and stained with iodine vapor. Incorporation of label into lipids was determined after scintillation counting and normalization to a [$^{14}$C] cholesterol internal standard and cell dry weight. For each assay, minimums of three independent strains of each genotype were used. Statistical analysis was performed using paired T test.

Analysis of DAG accumulation by steady state labelling: Cells were grown for 18-25 hrs to mid-log phase or early stationary phase in media containing 1 μCi/ml [$^3$H]oleate (9). Cells were harvested and lipids were extracted, separated, visualized and quantified as described above.

Isolation of microsomes: Microsomes were isolated as described (27). Briefly, wild type and mutant strains were cultivated in 1 liter YES medium at 30° C. overnight to log phase. Cells were collected through centrifugation. The pellets were washed with dH$_2$O, resuspended and incubated at 0.5 g wet wt/ml in 0.1M Tris SO$_4$ (with 10 mM DTT) at room temperature for 10 minutes. Cells were harvested, washed once with 1.2 M sorbitol, and resuspended at 0.15 g wet wt/ml in 1.2 M sorbitol (with 20 mM K$_3$PO$_4$ and 0.5 mg/ml lyticase), pH 7.2. Spheroplasts were formed after a 90 minute incubation at 30° C. Cells were washed twice with 1.2 M sorbitol, resuspended and disrupted with 20 strokes in a Dounce homogenizer using a tight fitting pestle at 4° C. Homogenates were spun at 20,000 g for 30 min. The pellets were discarded. The supernatants were collected and spun at 100,000 g for 45 min. The final pellets containing microsomes were resuspended in 10 mM TrisCl pH 7.4. Protein concentrations were determined by a Bradford assay kit from Bio-Rad.

It vitro (microsomal) assay of DAG esterification: Enzyme activity was determined by the incorporation of [1-$^{14}$C] oleoyl-CoA, 1-stearoyl-2-[$^{14}$C] arachidonyl-sn-glycerol and 1-palmitoyl-2 [1-$^{14}$C] oleoyl phosphatidylethanolamines (PE) into TAG as described (9). Each standard assay was performed in triplicate in 150 mM Tris-HCl pH 7.8 and final volume was 200 μl, containing 80 μg microsomal proteins, 15 μM BSA, 150 μM DAG, 8 mM MgCl$_2$, 150 μM phosphatidylserine (PS)/phosphatidylethanolamines (PE) liposomes (1:1 molar ratio), and 50 μM oleoyl-CoA. All the assays were conducted at room temperature for 25 min. For PDAT assay, oleoyl-CoA was omitted while [$^{14}$C] PE was added in liposomes at different concentrations (0, 15, 30, 45, and 60 μM). For DGAT assay, [$^{14}$C] oleoyl-CoA was added at different concentrations (0, 5, 20, 25 and 50 μM). In the diacylglycerol transacylase assay, [$^{14}$C] DAG was added at 0, 7.5, 15, 35 and 70 μM, whereas MgCl$_2$ and BSA were omitted. In control assays, all components were the same except microsomes were removed. Reactions were stopped by the addition of 6 ml chloroform/methanol (2:1). Phase separation was induced by the addition of 1.2 ml water. 1 μl of [$^3$H] cholesterol and 15 μg triolein were added as an internal standard and carrier, respectively. The lipid-containing phase was dried with nitrogen and the lipids were dissolved in 100 μl choloroform for spotting on TLC plates. The plates were developed in hexane: diethyl ether:acetic acid (70:30:1) and TAG was quantified by scintillation counting.

Diacylglycerol kinase assay: The assay was conducted as described in the Biotrak assay reagents system (Amersham Biosciences). Wild type and DKO yeast cells were grown in YES medium to mid log phase and then treated with medium containing 0.8 mM palmitate or oleate. Cells were collected at different time points (0, 30, 60 and 120 minutes). DAG was extracted with other lipids and quantified through a phosphorylation reaction catalyzed by a bacterial DAG kinase.

Results

Experiment 1—Deletion of plh1+ and dga1+ resulted in a viable yeast cell without detectable TAG: To determine whether Plh1p and Dga1p are involved in TAG synthesis in the fission yeast, we generated Δplh1, Δdga1 single and Δplh1 Δdga1 double deletion (referred to as the DKO strain) mutants by homologous recombination. All mutants were viable at 16° C., 30° C. and 37° C. on rich or minimal media and on different carbon sources (data not shown). We were also unable to observe any obvious morphological changes in the DKO cells under light microscope.

To investigate whether cellular TAG mass was affected in these strains, cells were grown to mid-log phase and lipids were extracted, separated by thin layer chromatography (TLC) and stained by iodine vapor. While the TAG mass in each single deletion mutant was visually indistinguishable from that of the wild type cells, virtually no TAG mass could be seen for DKO cells (data not shown). The sterol ester mass was clearly visible for all mutants, ruling out a lipid extraction error for the DKO strain.

To further examine the ability of these strains to synthesize TAG, cells in log phase were pulse labeled with [$^3$H] oleate and its incorporation into TAG was measured (FIG. 1). No significant differences in oleate incorporation into TAG were detected between wild type and the Δdga1 mutant. However, TAG synthesis was decreased by nearly 50% due to the loss of Plh1p. Most notably, the double mutant was almost totally deficient in TAG synthesis. In contrast, sterol ester biosynthesis was normal in all mutants (data not shown).

Figure 2:
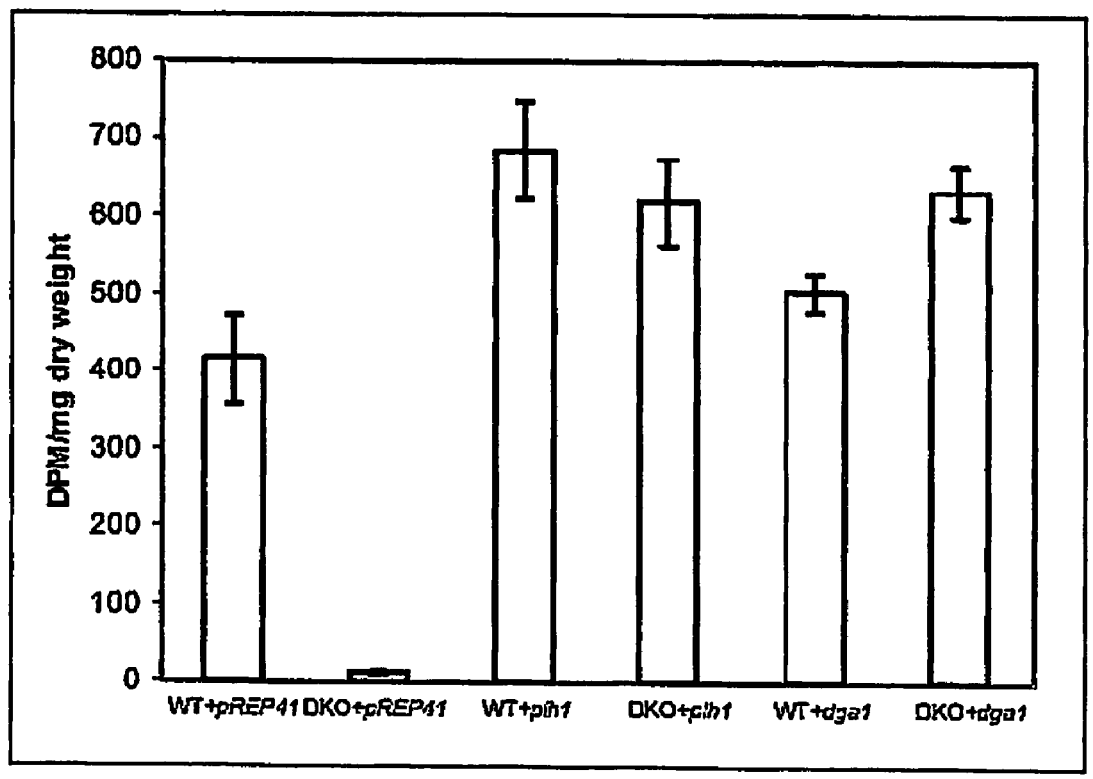
FIG. 2 is a graphical representation of results obtained from [$^3$H] oleate pulse labeling of WT and DKO strains transformed with control plasmid (pREP41), or expression plasmids plh1+ or dga1+.

To confirm that either Plh1p or Dga1p was sufficient for TAG synthesis, we overexpressed plh1+ and dga1+ in wild type and DKO strains. Both genes were placed under the control of a modified nmt1 promoter (21) and each gene was able to complement the TAG synthesis defect in the DKO mutant, indicating an overlapping function of these two genes (FIG. 2). Overexpression of plh1+ and dga1+ also caused a significant increase in TAG synthesis in WT and mutant strains, suggesting these genes could be regulated at the level of transcription. These results imply that TAG synthesis is mediated by two gene products in fission yeast while Plh1p plays a major role at log phase.

Figure 3:
FIG. 3 is a fluorescence micrograph of WT and DKO cells grown to early stationary phase and stained with 10 mg/ml Nile Red.
Figure 3:
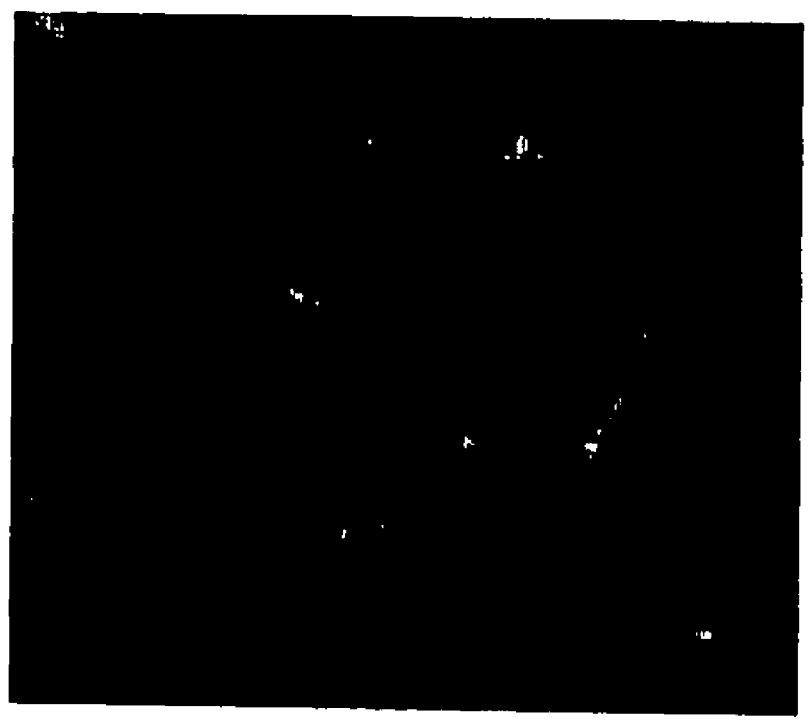

To further confirm the absence of TAG in the DKO strain, we treated yeast cells with Nile Red, a fluorescent dye with strong and specific affinity for neutral lipids (28). In both of the wild type and DKO cells, cytoplasmic fluorescent droplets could be seen in early stationary phase cultures. However, the number and intensity of the droplets observed in DKO cells was significantly less than those in wild type strains (FIG. 3).

Experiment 2—In vitro microsomal assays of DAG esterification: The results described above demonstrated the essential roles of Plh1p and Dga1p in TAG synthesis; however, they did not reveal the exact molecular function of these two proteins. Based on sequence homology and experimental data from previous studies (8, 9, 10, 11), it is highly likely that both of Plh1p and Dga1p carry out DAG esterification, with Dga1p functioning as an acyl-CoA DAG acyltransferase (DGAT) while Plh1p functioning as a phospholipid DAG acyltransferase (PDAT).

Figure 4A:
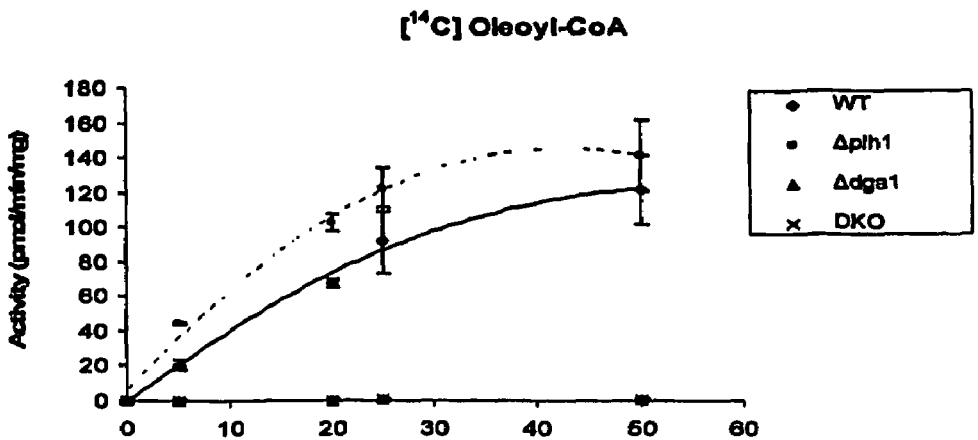
FIGS. 4A-C are graphical representations of results obtained from measuring DAG esterification activities using microsomes extracted from deletion strains grown to log phase, using WT microsome activity as 100%; substrates used were: A, 0-50 μM [1$^{14}$C] oleoyl-CoA and 150 mM 1,2-dioleoyl-sn-glycerol; B, 0-70 μM 1-stearoyl-2-[1-$^{14}$C] arachidonyl-sn-glycerol and 50 mM oleoyl-CoA; and C, 0-60 μM 1-palmitoyl-2 [1-$^{14}$C] oleoyl phosphatidylethanolamines and 150 μM 1,2-dioleoyl-sn-glycerol.
Figure 4B:
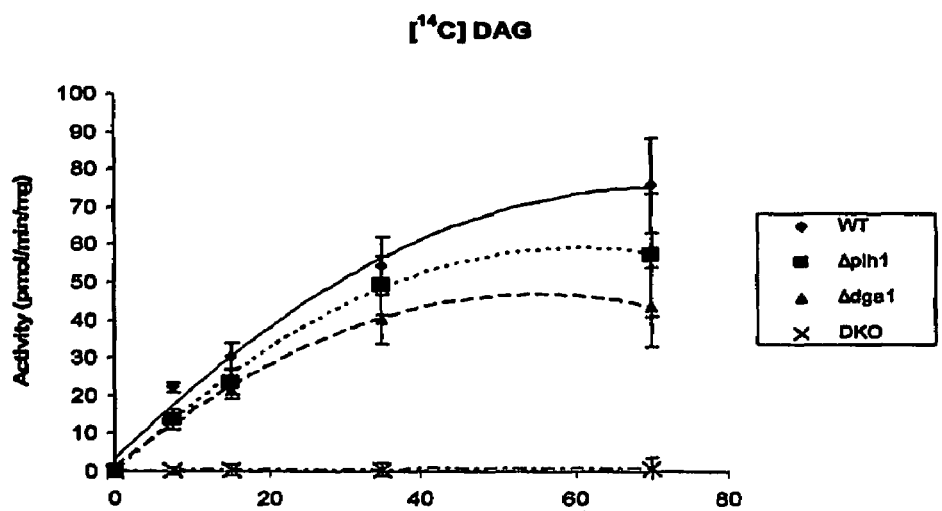
Figure 4C:
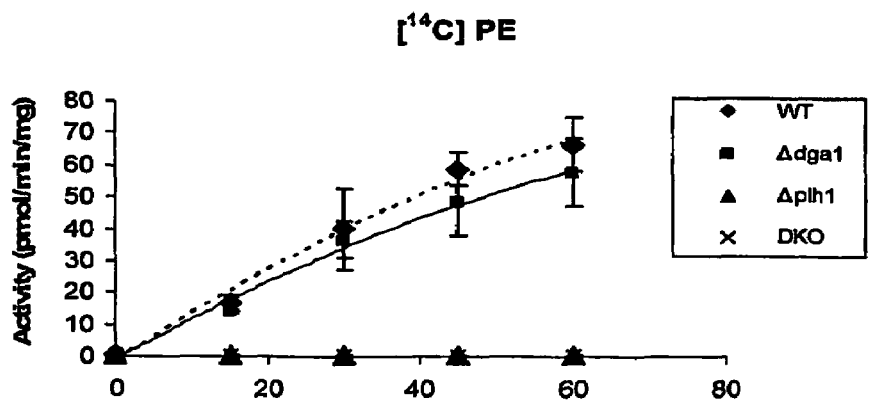

To confirm this hypothesis, we analyzed DAG esterification using microsomes prepared from the wild type and deletion mutant strains. When [$^{14}$C]oleoyl-CoA and unlabeled diacylglycerol were added to the microsomes, the DGAT activity in Δplh1 cells was significantly higher than the level in WT cells up to 25 mM oleoyl-CoA, whereas it was nearly undetectable in microsomes from Δdga1 and DKO cells (FIG. 4A). When [$^{14}$C]diacylglycerol and cold acyl-CoA were used, almost no DAG incorporation into TAG could be detected in the DKO strain. The Δdga1 microsomes showed about 50% DAG esterification activity of the normal microsomes, whereas the Δplh microsomes had similar activity as the wild type microsomes (FIG. 4B). When 1-palmitoyl-2 [1-$^{14}$C] oleoyl phosphatidylethanolamines (PE) and unlabeled DAG were added, microsomes from wild type cells and Δdga1 cells incorporated radiolabeled fatty acid into TAG at similar rates (FIG. 4C). This activity was absent in Δplh1 microsomes and in microsomes prepared from the DKO strain, indicating that Plh1p mediates esterification of DAG using the sn-2 acyl group of PE as the acyl donor. The substrate specificities of Plh1p and Dga1p were also investigated using the same in vitro assay system. Plh1p showed the best activity with PE, followed by phosphatidylcholine and phosphatidylinositol. Dga1p prefers palmitate over oleate (data not shown). Lastly, normal microsomes showed no incorporation of fatty acid from PE into sterol esters (data not shown), indicating that ergosterol is not a substrate for Plh1p under these assay conditions.

Experiment 3—Cells deleted for both plh1+ and dga1+ underwent apoptosis upon entering stationary phase: Schaffer and colleagues have recently demonstrated that TAG synthesis protected against fatty acid-induced lipotoxicity in Chinese hamster ovary (CHO) cells (12). Other recent studies also implicated a critical role for TAG synthesis in cell viability in *Drosophila* and in the oleaginous yeast (29, 30). Previous reports indicated that the sole growth phenotype in budding yeast cells without neutral lipids was a prolonged lag phase with no significant change of growth in exponential or stationary phases.

We examined the growth properties of wild type and DKO *S. pombe* cells and found that when stationary phase cells with the same $OD_{595}$ value were used to start a growth culture, there was indeed a significant delay in the onset of log phase for DKO cells; however, when log-phase cells were used to start the culture, there was no such lag phase (data not shown). These data suggest that, among other possibilities, most of the double mutant cells in the stationary phase could not be revived.

Figure 5:
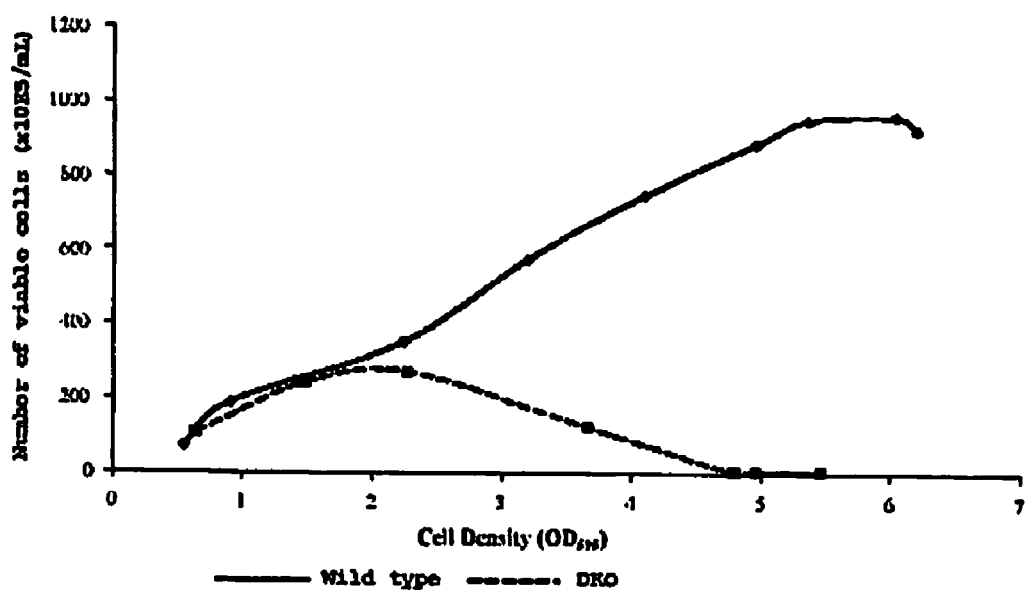
FIG. 5 depicts cell viability of WT and DKO strains at various cell densities.
Figure 6:
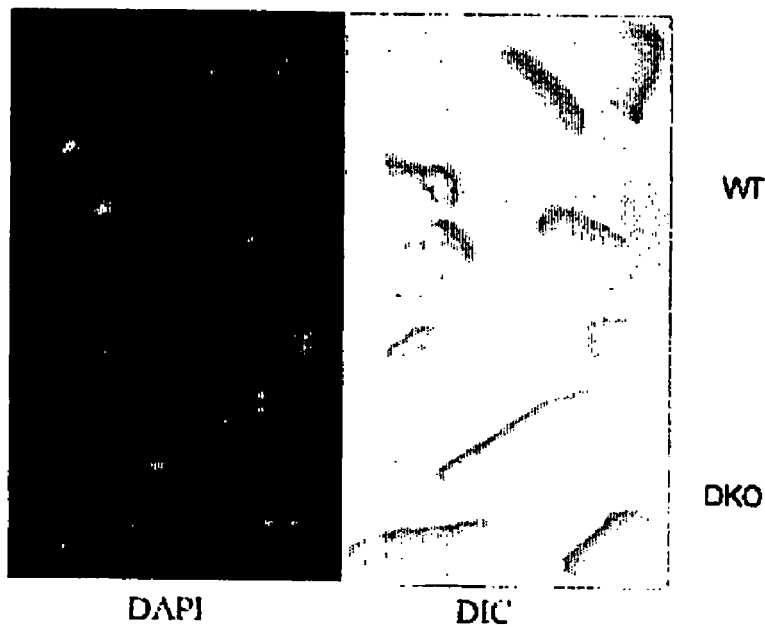
FIG. 6 is fluorescence ("FITC") and phase contrast ("DIC") micrographs of WT and DKO cells grown to early stationary phase and DAPI stained.

To test this hypothesis, a colony forming assay was performed (FIG. 5) and as expected, most of DKO cells started losing viability upon entry into stationary phase. In addition, when the stationary phase cells were stained with DAPI, remarkable nuclear DNA fragmentation was detected in the majority of the DKO cells, while no such fragmentation was observed in any WT cells (FIG. 6).

Figure 7:
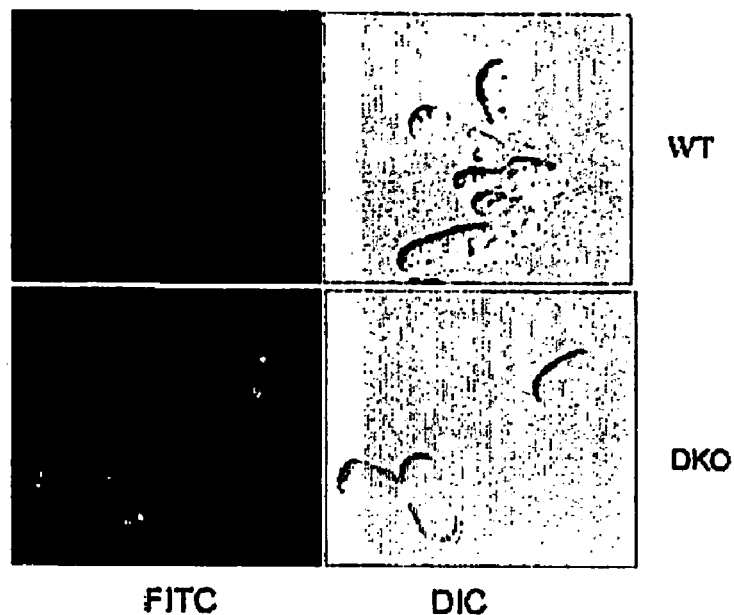
FIG. 7 is fluorescence and phase contrast micrographs of WT and DKO cells grown to early stationary phase and TUNEL stained.

The mechanisms of this stress-induced cell death were further investigated by the TUNEL assay. Cleavage of DNA during apoptosis produces free 3'OH termini, which can be effectively labeled by fluorescently tagged nucleotides in a process catalyzed by terminal deoxynucleotidyl transferase (TdT). It was found that at early stationary phase, DNA fragmentation occurs in the majority (over 50%) of mutant cells, as seen by the extensive TUNEL reaction (FIG. 7). This extensive labeling was not observed in any of the wild-type cells. Log-phase cells in general did not show positive labelling, a result that is consistent with the findings that in the logarithmic growth phase, the double mutant has a comparable viability with the wild-type strain.

Figure 8:
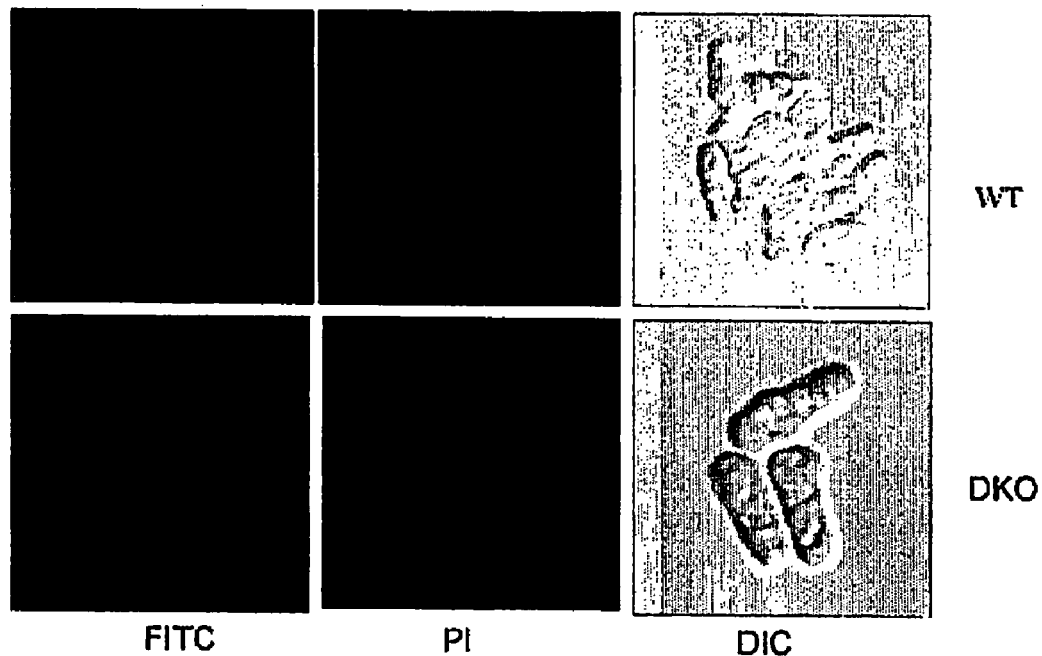
FIG. 8 is fluorescence and phase contrast micrographs of WT and DKO cells grown to early stationary phase and stained with FITC-labeled annexin V and propidium iodine (PI)

The TUNEL positive phenotype suggested to us that the DKO cells could undergo apoptotic cell death when starved; therefore, we looked for more apoptotic markers. In mammalian and *S. cerevisiae* cells, exposure of phosphatidylserine (PS) at the outer leaflet of the plasma membrane is an early marker for apoptosis (31). To test whether the same process occurs in *S. pombe*, spheroplasts of WT and DKO cells derived from stationary phase cultures were incubated with FITC-labeled annexin V. As shown in FIG. 8, strong fluorescence could be seen in the periphery of about 10% of mutant cells, suggesting that phosphotidylserine is indeed exposed to the outer leaflet of plasma membrane. Membrane integrity was intact as propidium iodine (PI) was excluded from most of the annexin V positive cells. In contrast, no FITC fluorescence was observed for WT cells.

Production of reactive oxygen species (ROS) represents another prominent marker for apoptosis in yeast (26). We treated WT and DKO cells with dihydroethidium, which can be oxidized by ROS to fluorescent ethidium. Over 50% of mutant cells at stationary phase fluoresced strongly, whereas WT cells showed little or no fluorescence (FIG. 9), neither did exponentially growing cells (not shown).

Experiment 4—DAG accumulates in DKO cells and triggers apoptosis: Loss of viability, nuclear DNA fragmentation, exposure of PS and generation of reactive oxygen species lend strong support to the conclusion that these DKO cells underwent apoptosis upon nutrient starvation. Apoptosis has been shown to exist in the unicellular organism *S. cerevisiae*, with ROS playing a central regulatory role and the newly identified caspase homolog Yca1p as a possible central executioner (32, 33). However, how internal and environmental cues stimulate the production of ROS is largely unknown and whether there are other factors or pathways which might function independently of ROS or caspase to regulate apoptosis in yeast remains to be explored.

We sought to understand the mechanism of this novel form of apoptotic cell death caused by the inability of DKO cells to produce TAG. *S. cerevisiae* cells begin accumulating neutral lipids upon exiting logarithmic growth phase, probably as a result of phospholipids remodeling by altering the activities of phosphatidate phosphotases (34). Due to the loss of DAG esterification capability in DKO cells, DAG and long chain fatty acids, two signaling molecules and major substrates for TAG synthesis, could accumulate upon entry into stationary phase and induce apoptosis.

Figure 10A:
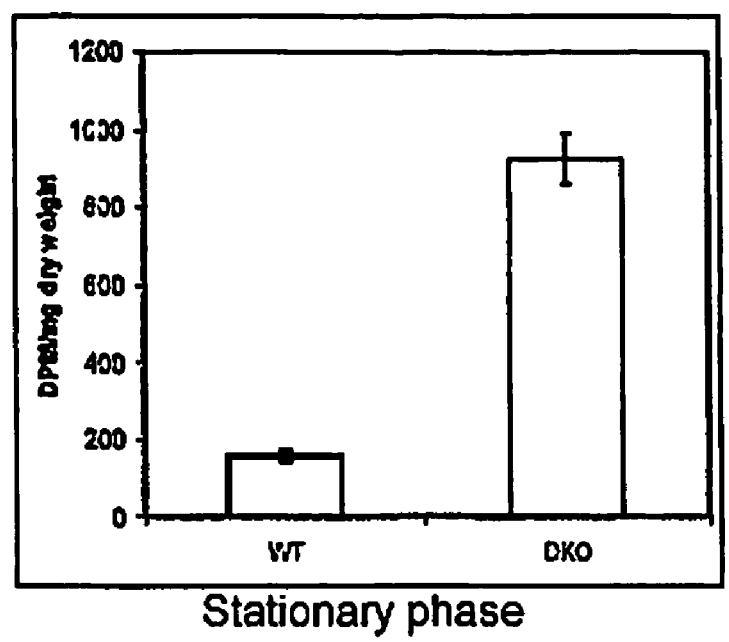
FIGS. 10A-B illustrate the results of DAG quantification using thin layer chromatography at A, log phase and B, early stationary phase for WT and DKO cells labeled with [$^3$H] acetate.
Figure 10B:
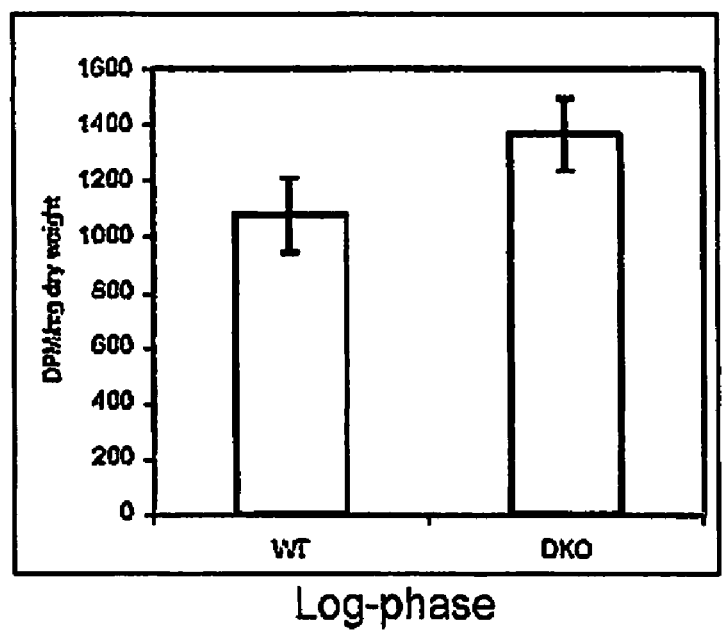

We therefore examined the quantity of DAG, palmitic and oleic acids, in WT and DKO strains. Steady state labeling experiments showed that there was almost 300% more DAG in DKO cells than in WT cells at early stationary phase (FIGS. 10A and 10B), whereas there was little difference between the two strains at log phase. Surprisingly, no significant differences in free fatty acid levels between WT and DKO cells were observed as measured by GC-MS (not shown). This result suggests that accumulation of DAG might be the key to the death of DKO cells at stationary phase. The free fatty acids might have been incorporated into such molecules as DAG, ceramide, phospholipids and sterol esters etc. We reasoned that if the apoptotic cell death of the double mutant cells was indeed caused by accumulation of DAG upon entry into stationary phase, we should be able to kill exponentially growing cells with exogenously added DAG.

Figure 11:
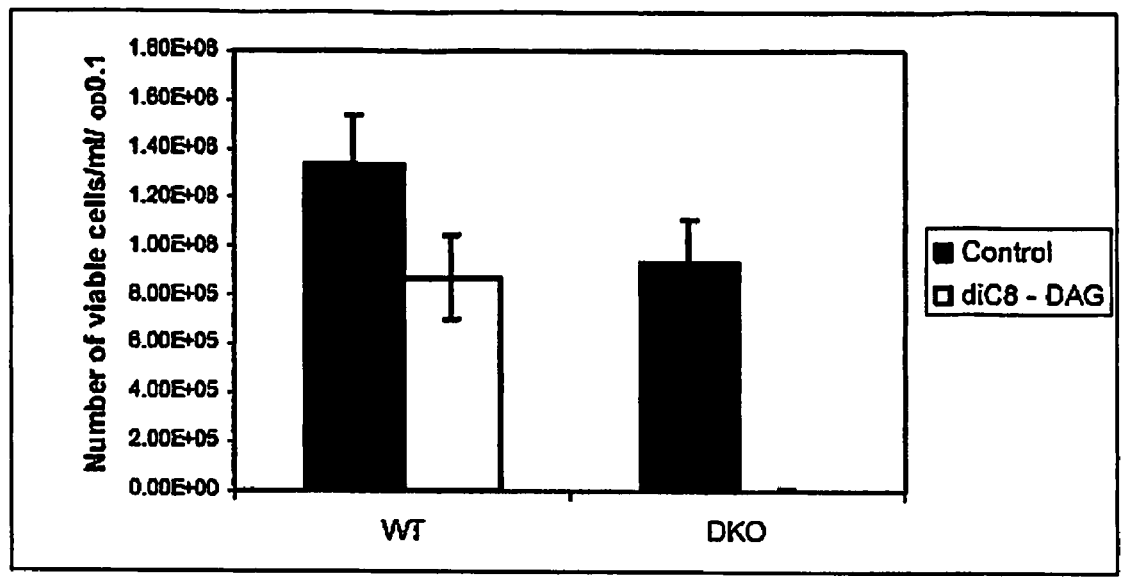
FIG. 11 demonstrates the results of a cell viability assay using WT and DKO strains grown to early log phase and treated with 0.2 mM 1,2-dioctanoyl-sn-glycerol ("diC8 DAG") for 2 hours.
Figure 12:
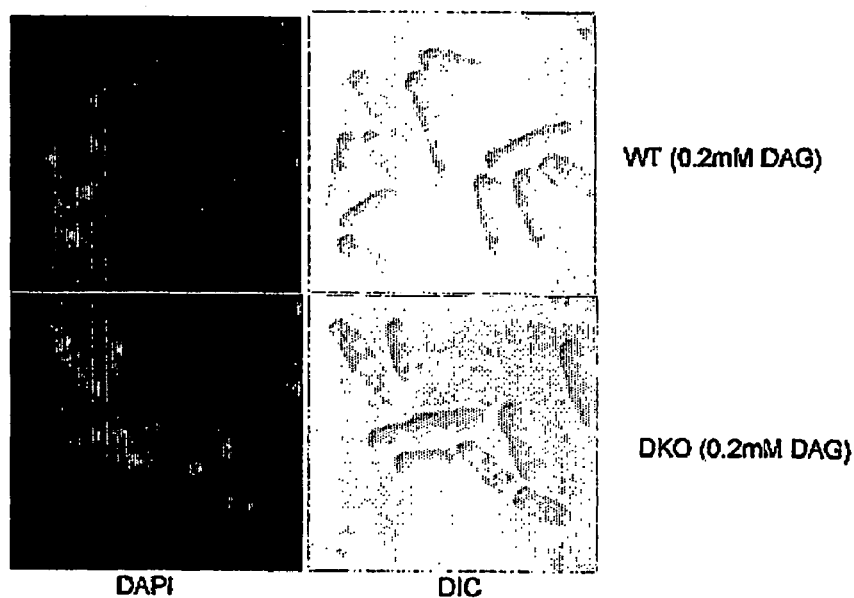
FIG. 12 is fluorescence and phase contrast micrographs of WT and DKO cells grown to early log phase and treated with 0.2 mM diC8 DAG for 2 hours and DAPI stained.
Figure 13:
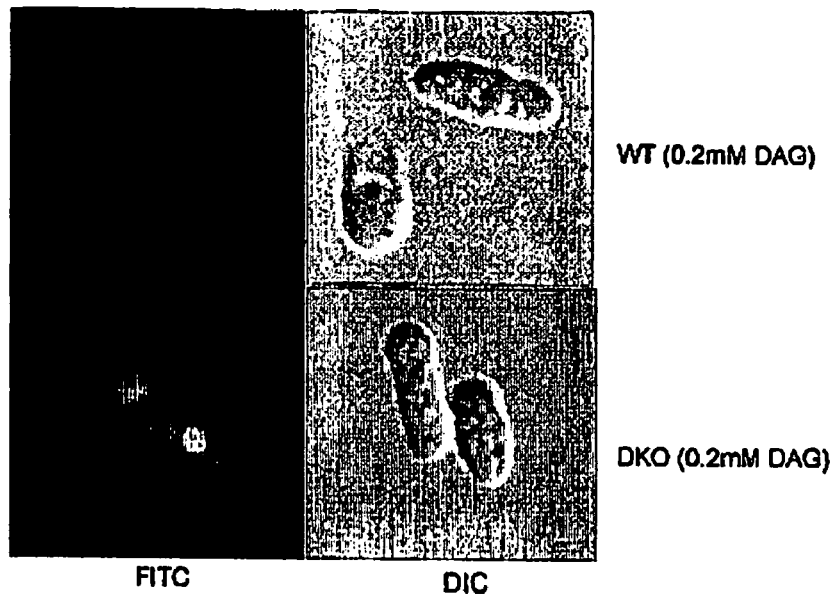
FIG. 13 is fluorescence and phase-contrast micrographs of WT and DKO cells grown to early log phase and treated with 0.2 mM diC8 DAG for 2 hours and TUNEL stained.

We therefore treated log-phase cells with a membrane permeable DAG analog called diC8 DAG (1,2-dioctanoyl-sn-glycerol). Early log phase cells were treated with various concentrations of diC8 DAG and for 0-3 hours. As expected, prominent nuclear DNA fragmentation and cell death were observed in the DKO strain, but not the wild type. The percentage of cell& showing DNA fragmentation generally increases with time (up to 3 hours) and concentration of diC8 DAG (up to 0.3 mM). The results of cells treated with 0.2 mM diC8 DAG for 2 hours are shown in FIGS. 11-13.

Experiment 5—Fatty acids induce apoptosis through DAG: To further investigate the possible role of DAG in yeast apoptosis, we focused our attention on free fatty acids. We reasoned that if DAG is indeed the apoptosis-inducing molecule in the DKO cells, treating the cells with free fatty acids would also trigger apoptosis because excessive free fatty acids would increase the production of, among other molecules, DAG.

Figure 14:
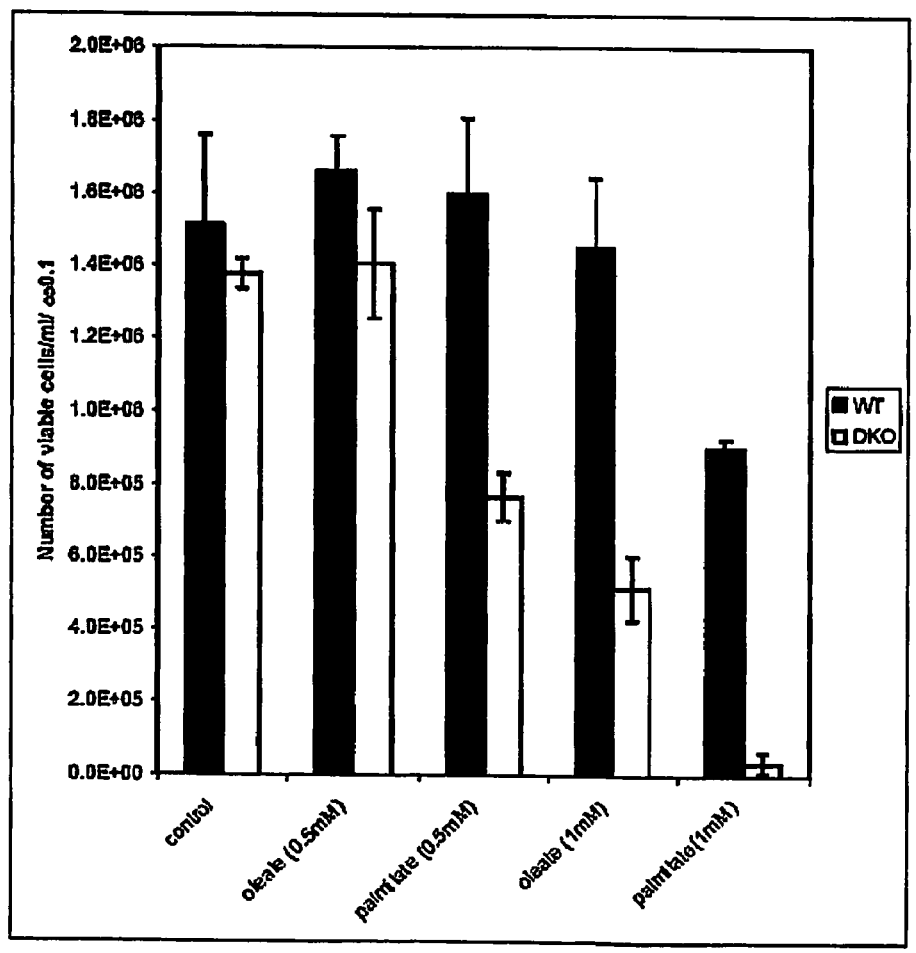
FIG. 14 illustrates the results of a cell viability assay of cells grown to early log phase and treated with various concentrations of oleate or palmitate for two hours.
Figure 15:
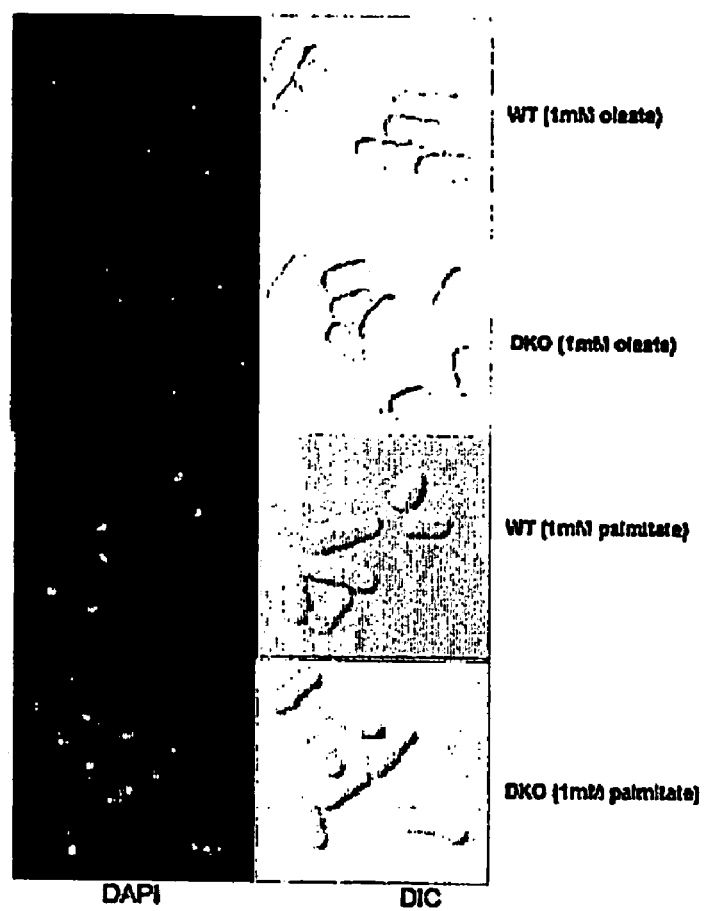
FIG. 15 is fluorescence and phase contrast micrographs of WT and DKO cells grown to early log phase and treated with oleate or palmitate for two hours and DAPI stained.
Figure 16:
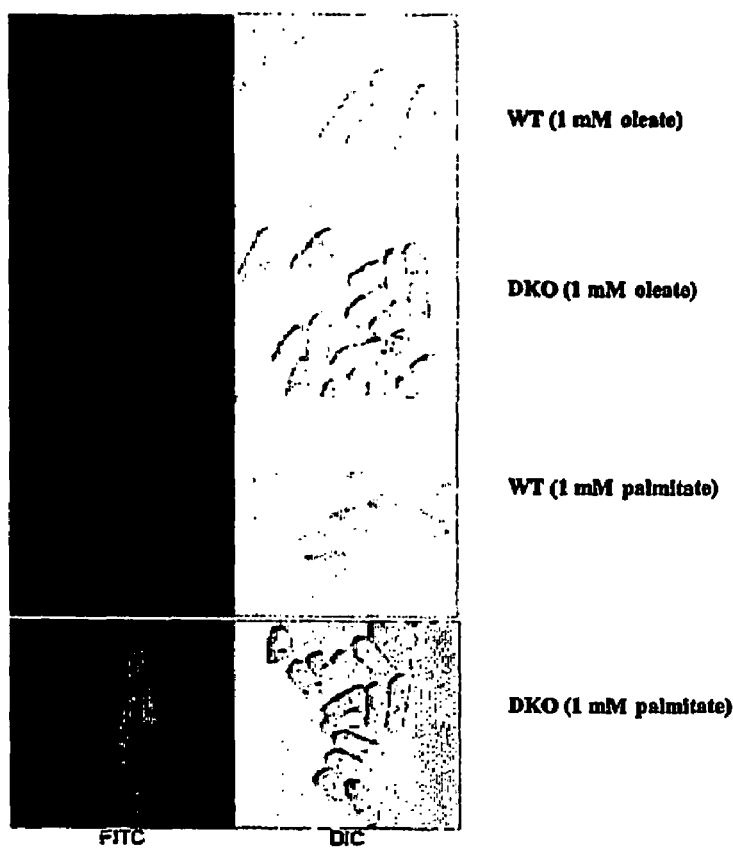
FIG. 16 is fluorescence and phase contrast micrographs of WT and DKO cells grown to early log phase and treated with oleate or palmitate for two hours and TUNEL stained.

We treated WT and DKO cells with palmitate and oleate and not surprisingly, both of them caused the DKO cells to undergo apoptosis (FIGS. 14-16).

To prove that the fatty acids-induced apoptosis is caused by DAG, we first measured cellular DAG level after fatty acids were added to growth media Since steady state labeling would not be a feasible method to estimate DAG in this case, a DAG kinase kit was used instead to estimate cellular DAG after cells were incubated with 0.8M palmitate or oleate for 2 hours. As expected, the DAG level in DKO cells increased from 1 nmol/mg dry weight before addition of palmitate to 3.5 nmol/mg dry weight after a 2-hour incubation. In wild type cells, the change was mild (from 1 to 1.5 nM/mg dry weight). With oleate, there was a less but significant increase in DAG level (from 1 to 2.5 nM/mg dry weight) in DKO cells. The different effects of palmitate or oleate could be due to substrate preference of glycerol-3 phosphate acyltransferases in S. pombe. In fact, it has been demonstrated in S. cerevisiae that 16-carbon fatty acids are preferred substrates of Gat2p, one of the two newly identified enzymes that control the initial steps of glycerolipid synthesis (35).

Figure 18:
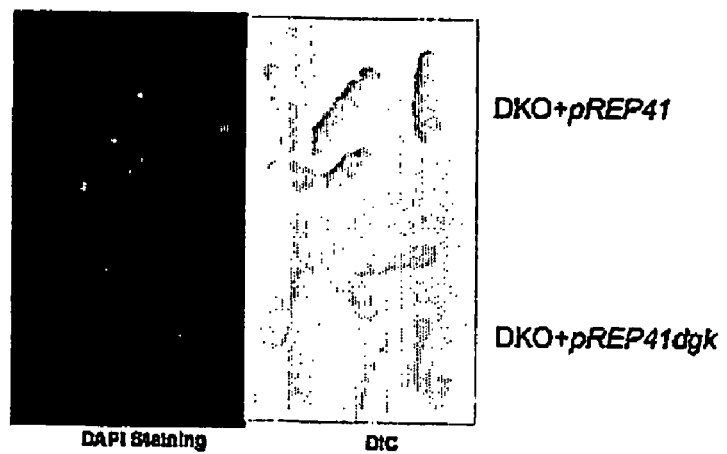
FIG. 18 is fluorescence and phase contrast micrographs of DKO cells transformed with pREP41 or pREP41dgk, grown to early log phase and treated with palmitate and DAPI stained.
Figure 19:
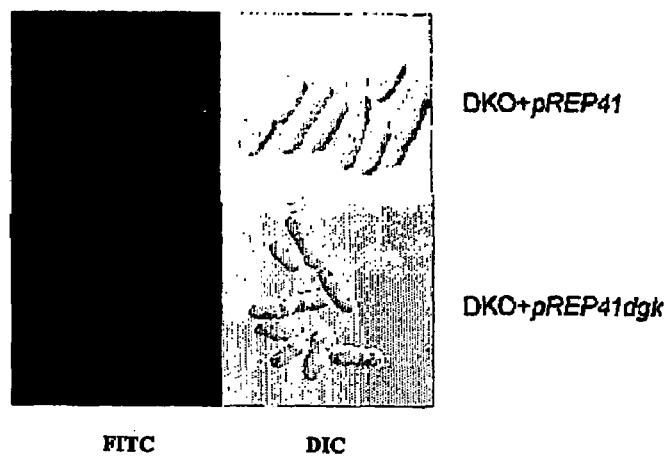
FIG. 19 is fluorescence and phase contrast micrographs of DKO cells transformed with pREP41 or pREP41dgk grown to early log phase and treated with palmitate and TUNEL stained.
Figure 17:
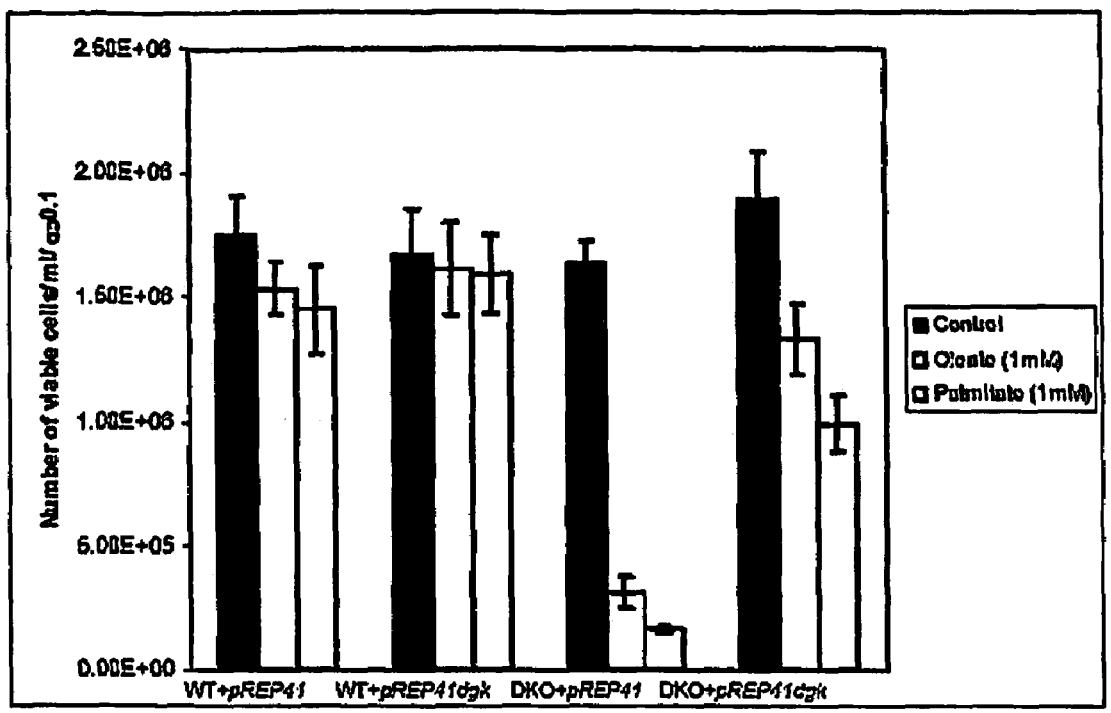
FIG. 17 illustrates the results of a cell viability assay of cells transformed with control plasmid (pREP41) or a plasmid expressing DAG kinase pREP41dgk) and grown to early log phase, then treated with oleate or palmitate.

To further prove that fatty acids cause apoptosis through increased de novo synthesis of DAG, we tested whether removal of DAG could attenuate or reverse palmitate/oleate-induced apoptosis. A bacterial DAG kinase (DGK) was expressed in the double deletion strain under the control of a modified nmt1 promoter (21, 22). The expression resulted in a DAG kinase activity of 35 pmol/min/mg as determined by ATP ($\gamma$-$^{32}$P) incorporation into phosphatidic acid (PA), three fold higher than basal activity. As shown in FIG. 17, nearly 60 percent of DKO cells survived as a result of DGK expression while only a 5% survival rate was observed in cells containing the empty plasmid. Further evidence was obtained by DAPI staining and the TUNEL assay. Significantly fewer cells with DGK expression showed DNA fragmentation and positive TUNEL reaction (FIGS. 18 and 19). Based on these results, we could conclude that the apoptosis inducing effect of fatty acids is mediated, if not exclusively, by DAG.

Figure 20:
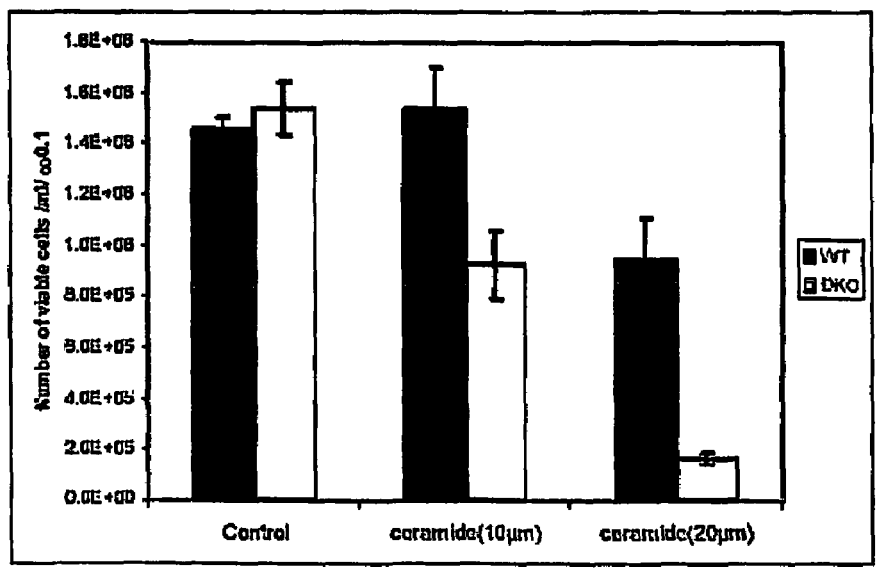
FIG. 20 illustrates the results of a cell viability assay of cells grown to early log phase and treated with various concentrations of C2 ceramide for two hours.
Figure 21:
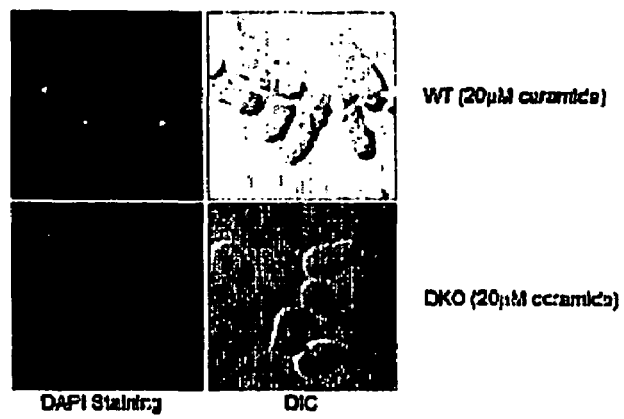
FIG. 21 is fluorescence and phase contrast micrographs of WT and DKO cells grown to early log phase and treated with C2 ceramide for two hours and DAPI stained.
Figure 22:
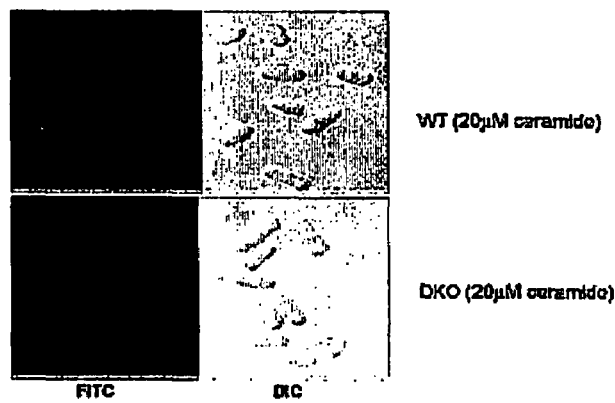
FIG. 22 is fluorescence and phase contrast micrographs of WT and DKO cells grown to early log phase and treated with C2 ceramide for two hours and FITC stained.

Palmitate can also induce de novo synthesis of sphingolipids, some of which are potent pro-apoptotic molecules in other experimental systems. To determine whether dihydrosphingosine (DHS), phytosphingosine (PHS), or ceramide plays a role in palmitate-induced apoptosis, WT and DKO cells were treated with various concentrations of DHS, PHS or C2-ceramide for different periods of time (0-3 hours). These compounds could kill S. pombe cells at high concentrations; however, no DNA fragmentation was observed (only the effect of a two-hour treatment by 10 µM and 20 µM C2-ceramide is shown in FIGS. 20-22). These data are consistent with previous findings that ceramide cause cell cycle growth arrest, not apoptosis, in S. cerevisiae (24).

We also examined the effect of fumonisin B1 (inhibitor of ceramide synthase) and myriocin (inhibitor of serine palmitoyl transferase) on the growth of double deletion cells treated with 0.8 mM of palmitate. As expected, no rescue of apoptosis was observed and as a matter of fact, more cells underwent apoptosis in the presence of fumonisin B1 or myriocin (data not shown). These results suggest that sphingolipids are not involved in palmitate induced apoptosis in S. pombe and when sphingolipid synthesis is blocked, palmitate could be channeled to other pathways, such as the glycerolipid pathway.

Experiment 6—Generation of ROS is essential to lipoapoptosis while deletion of a caspase homolog has no effect: Oxidative stress has been shown to act as a key regulator of apoptosis in S. cerevisiae (26) and in other organisms (36, 37). In addition, palmitate-induced lipoapoptosis in CHO cells required increased production of ROS (38). We therefore sought to determine whether generation of ROS is required for the death of DKO cells.

Figure 9:
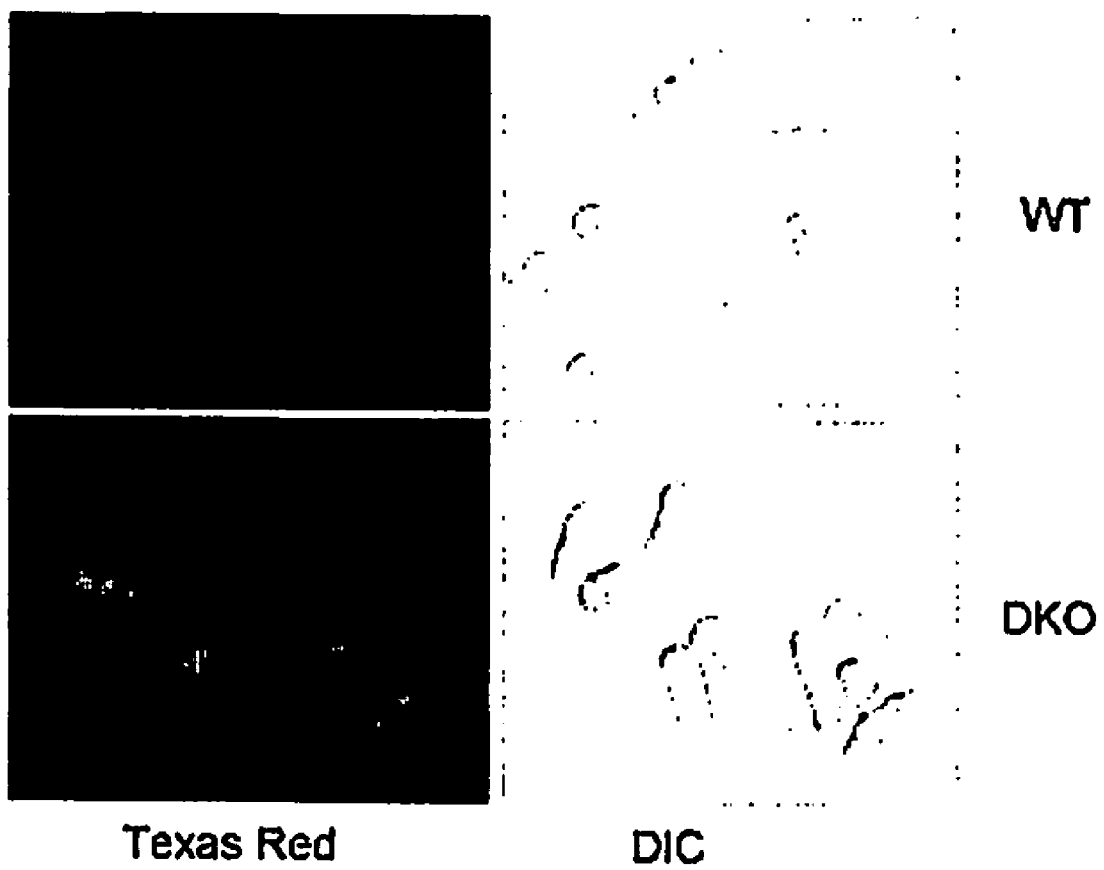
FIG. 9 is fluorescence and phase contrast micrographs of WT and DKO cells grown to early stationary phase and incubated with dihydroethidium (Texas Red) for 10 minutes.

We have shown that ROS were generated when DKO cells entered stationary phase (FIG. 9). Incubation of log phase cells with DAG (not shown), oleate (not shown) or palmitate (FIG. 25) also induced dramatic ROS production.

Figure 23:
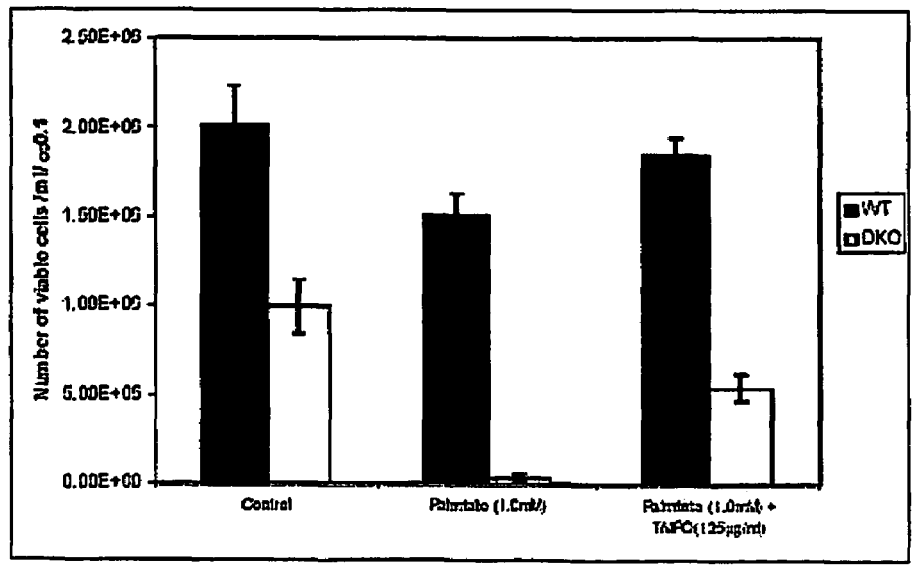
FIG. 23 illustrates the results of a cell viability assay of cells grown to early log phase and pretreated with or without 125 µg/ml of TMPO for two hours and then incubated with 1 mM palmitate for two more hours.
Figure 24:
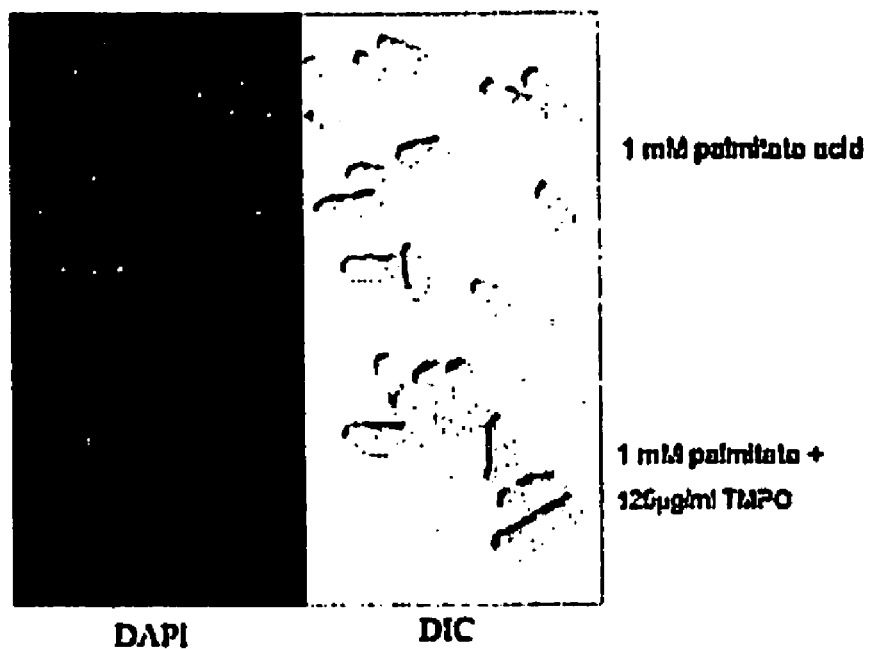
FIG. 24 is fluorescence and phase contrast micrographs of DKO cells grown to early log phase and pretreated with or without 125 µg/ml of TMPO for two hours and then incubated with 1 mM palmitate for two more hours and DAPI stained.
Figure 25:
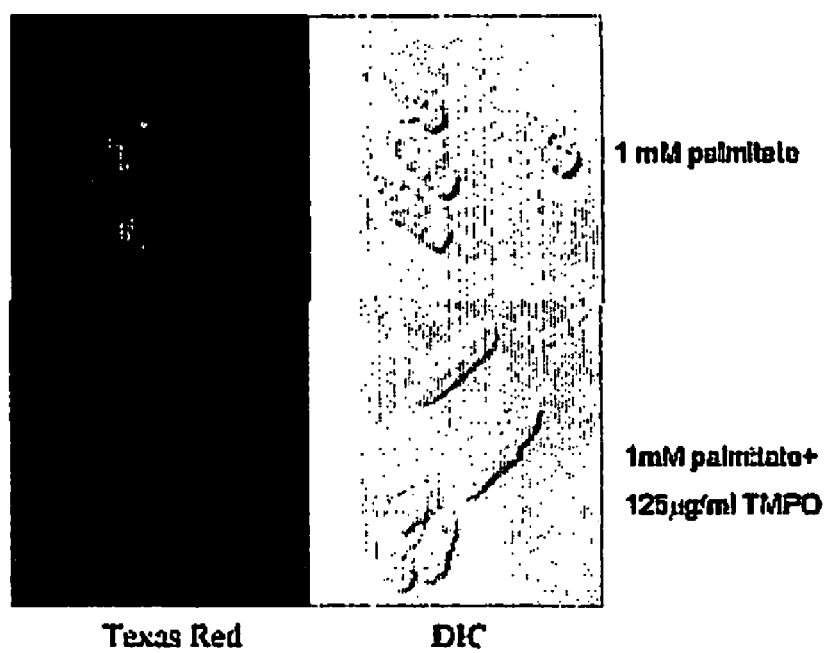
FIG. 25 is fluorescence and phase contrast micrographs of DKO cells grown to early log phase and pretreated with or without 125 µg/ml of TMPO for two hours and then incubated with 1 mM palmitate for two more hours and treated with Texas Red.

To determine whether ROS are required for lipoapoptosis in our yeast strain, we examined the effect of the free radical spin trap TMPO on cell viability and DNA fragmentation. Mutant cells were pretreated with TMPO for 2 hours before 1 mM palmitate was added for 2 hour. As shown in FIGS. 23 to 25, TMPO could effectively scavenge ROS (FIG. 25) and prevent DNA fragmentation (FIG. 24) and cell death (FIG. 23). The recent discovery of Yca1p, a yeast caspase homolog in S. cerevisiae, has generated much interest and excitement about regulators of apoptosis in yeast. We identified a Yca1 homolog in S. pombe (GeneDB systematic name: SPCC1840.04) and named it pca1+, for pombe caspase 1. A triple deletion strain (Δdga1 Δplh Δpca1, referred to as the TKO strain thereafter) was created and surprisingly, no difference in the degree of cell death and DNA fragmentation was observed between the DKO and TKO strains when cells were grown to stationary phase or when log phase cells were treated with DAG or fatty acids (data not shown). Adding caspase inhibitor zVADfmk also failed to prevent cell death and DNA fragmentation in our experimental systems (data not shown). These results suggest that the Pca1p or caspase does not play an essential role in lipoapoptosis in the fission yeast.

Experiment 7—Screening for compounds that inhibit or prevent fatty acid-induced lipoapoptosis: Commercially available compounds, including the 280,000 compounds approved for clinical use by the US Food and Drug Administration (FDA), or traditional herbal medicines that have been used as hypoglycemic and hypolipidemic agents, may be screened as follows. The compound to be tested may be added to yeast (DKO cells) cultures that have been treated to undergo lipoapoptosis, either by addition of about 1 mM palmitate, or by nutrient starvation, for example by culturing yeast cells in water or in a medium without glucose, in 96-well plates. A colony-forming assay will be performed to determine the viability of treated cells. If a significant recovery is observed after addition of a compound, the results may be confirmed by DAPI staining and the TUNEL assay. Compounds identified by this method may be further tested in other model systems, for example in animal models such as fa/fa diabetic rats.

Experiment 8—screening for compounds that inhibit or prevent TAG synthesis: Deletion of the DGAT1 gene in mouse caused resistance to diet-induced obesity (Smith et al., 2000). Therefore, inhibitors of DGAT1 could be effectively used to treat human obesity. To date, no such inhibitors exist. The yeast strains of the present invention offer an efficient way to screen for inhibitors against mammalian enzymes involved in TAG synthesis. The enzyme of interest, for example, human DGAT can be cloned into an appropriate expression vectors and introduced into the DKO cells, which have zero background DGAT activity. Oleate incorporation experiments as described above can be performed to confirm that the ectopically expressed human enzyme of interest is active in the yeast strain.

Once confirmed, a high throughput screening can be carried out to identify compounds that inhibit the activity of mammalian enzymes as follows: lipoapoptosis is induced in DKO yeast cells expressing a mammalian DGAT that have been incubated with a compound that is to be tested. Death by lipoapoptosis is used as the assay endpoint, which indirectly measures inability to synthesize TAG, since cell viability is more readily and quickly assayed than incorporation of labelled substrate into TAGs, and is therefore more amenable to high throughput screening of a large number of compounds for inhibition of mammalian DGAT. Palmitate alone effectively kills DKO yeast cells, which have no DGAT activity, by apoptosis. With a functional mammalian DGAT, the DKO cells will survive palmitate treatment. However, if the test compound inhibits the activity of the mammalian DGAT, the yeast cells will lose viability after treatments with palmitate. Once identified, the kinetics and specificity of the particular compounds having an inhibitory effect may be further tested in vitro.

Figure 26:
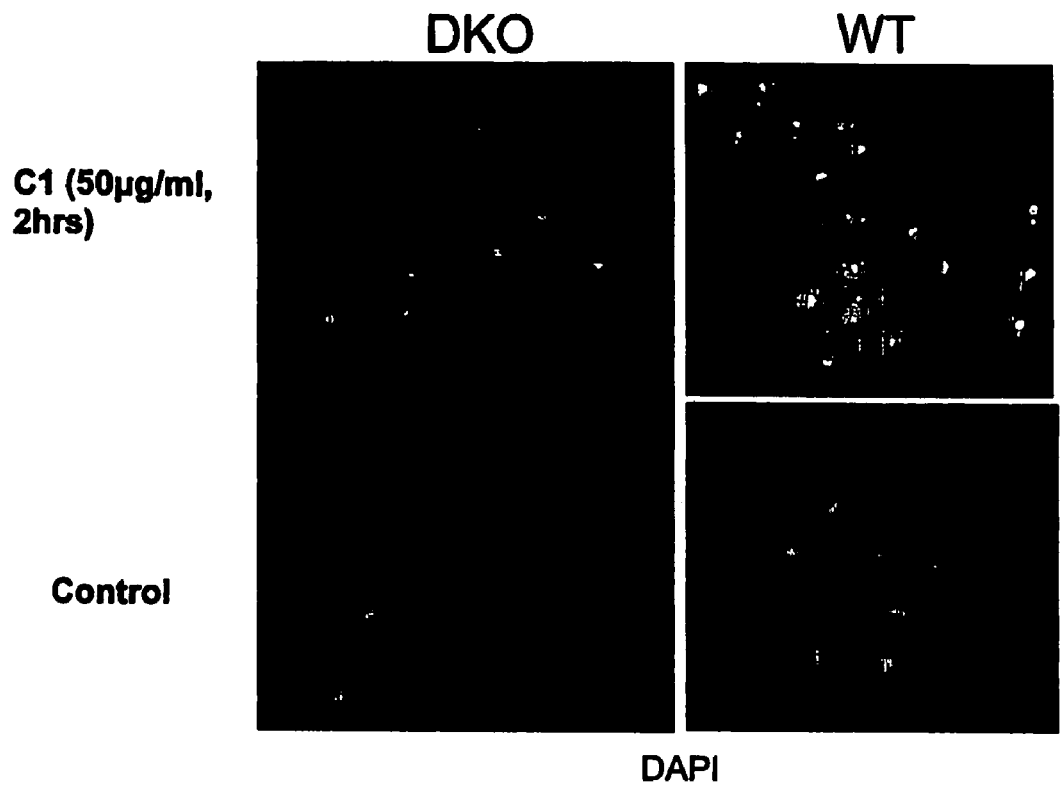
FIG. 26 is fluorescence micrographs of DKO and WT cells grown to early log phase and treated with compound C1 for two hours and DAPI stained.
Figure 27:
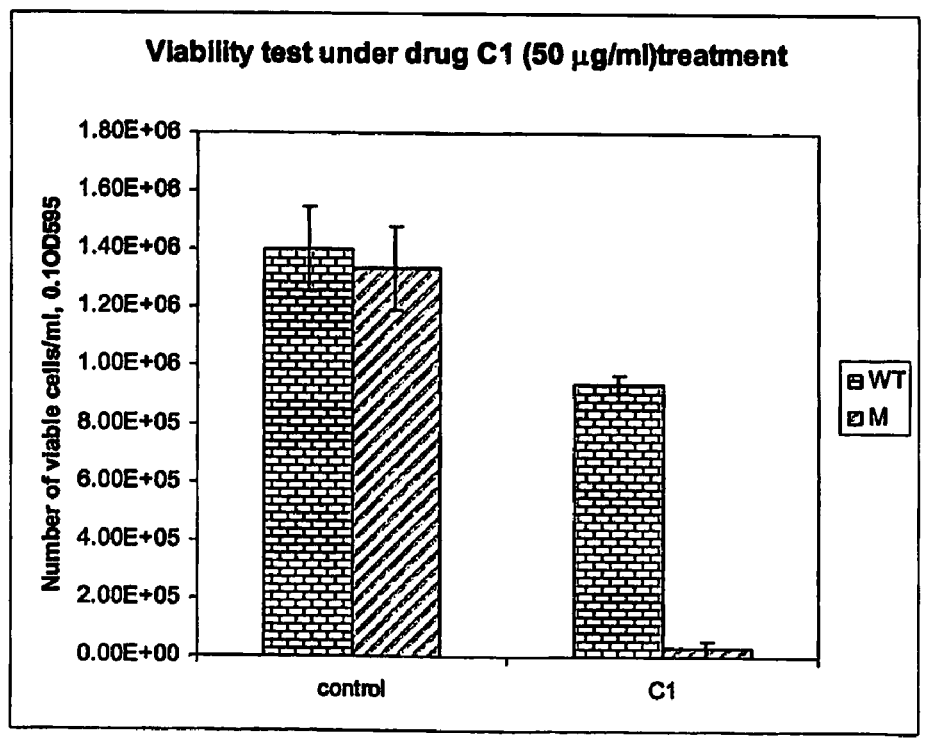
FIG. 27 illustrates cell viability of WT and DKO ("M") untreated cultures and cultures treated with compound C1, as measured by a colony forming assay.
Figure 28:
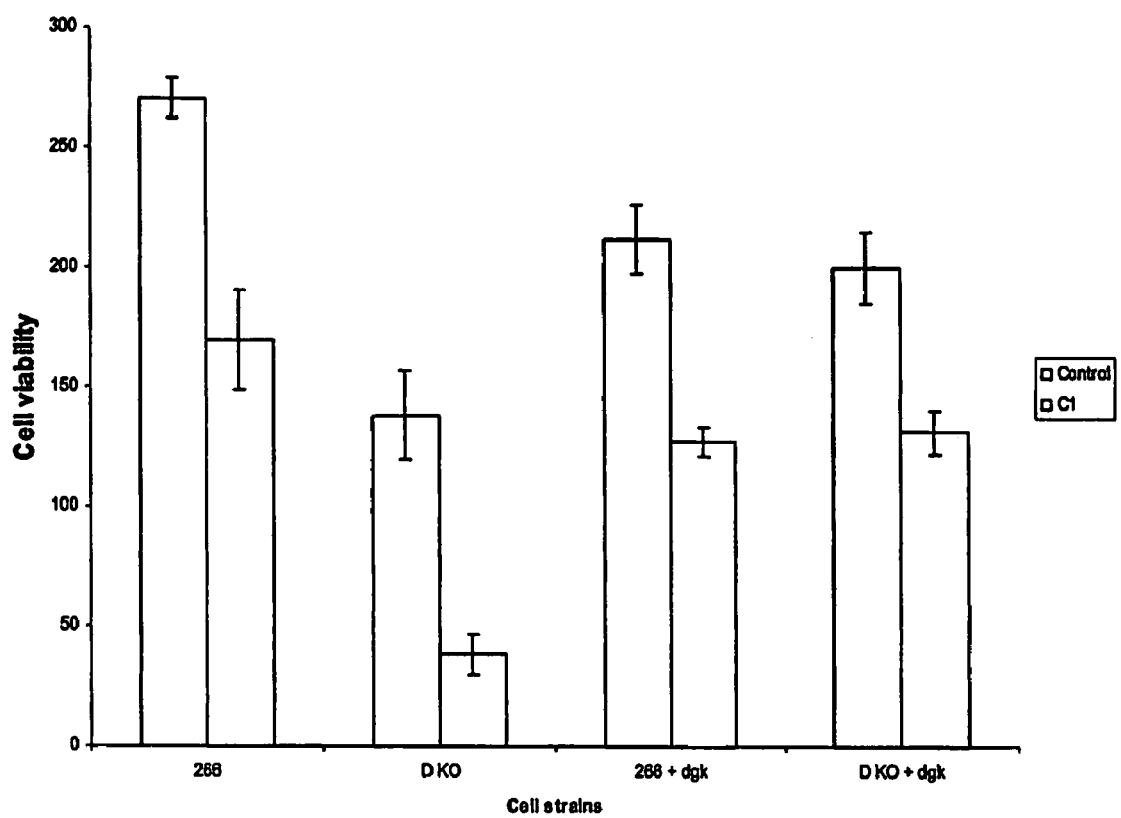
FIG. 28 illustrates the ability of expressed DAG kinase to rescue the DKO strain from lipoapoptosis induced by treatment with C1 (266=WT).

Alternatively, lipoapoptosis may be induced by incubation with other compounds known to induce lipoapoptosis, such as compound C1 (developed by A/P Shazib Pervaiz, Department of Physiology, National University of Singapore). FIGS. 26 and 27 demonstrate the ability of C1 to kill the DKO strain after incubation for 2 hours at a concentration of 50 μg/ml. The expression of DAG kinase ("dgk"), which converts DAG to phosphatidic acid is able to rescue the DKO strain from lipoapoptosis (FIG. 28; 266=wildtype strain).

Once candidate compounds have been identified that inhibit the activity of the expressed mammalian DGAT, the inhibitory effect may be confirmed by measuring the incorporation of labelled substrate, such as [$^3$H] oleate, into TAG, by methods such as those described above, such as total cellular lipid extraction and separation by thin layer chromatography.

As can be understood by one skilled in the art, many modifications to the exemplary embodiments described herein are possible. The invention, rather, is intended to encompass all such modification within its scope, as defined by the claims.

REFERENCES

1. Farese, R. V., Jr., Cases, S., and Smith, S. J. (2000) *Curr. Opin. Lipidol.* 11, 229-234
2. Bell, R. M., and Coleman, R. A. (1980) *Annu. Rev. Biochem.* 49, 459-487
3. Cases, S., Smith, S. J., Zheng, Y.-W., Myers, H. M., Lear, S. R., Sande, E., Novak, S., Collins, C., Welch, C. B., Lusis, A. J., Erickson, S. K, and Farese, R. V., Jr. (1998) *Proc. Natl. Acad. Sci. U.S.A.* 95, 13018-13023
4. Oelkers, P., Behari, A., Cromley, D., Billheimer, J. T., and Sturley, S. L. (1998) *J. Biol. Chem.* 273, 26765-26771
5. Cases, S., Stone, S. J., Zhou, P., Yen, E., Tow, B., Lardizabal, K D., Voelker, T., and Farese, R. V., Jr. (2001) *J. Biol. Chem.* 276, 38870-38876
6. Lardizabal, K. D., Mai, J. T., Wagner, N. W., Wyrick, A., Voelker, T., and Hawkins, D. J. (2001) *J. Biol. Chem.* 276, 38862-38869
7. Lehner, R., and Kuksis, A. (1993) *J. Biol. Chem.* 268, 8781-8786
8. Sandager, L., Gustavsson, M. H., Stahl, U., Dahlqvist, A., Wiberg, E., Banas, A., Lenman, M., Ronne, H., and Stymne, S (2002) *J. Biol. Chem.* 277, 6478-6482
9. Oelkers, P., Tinkelenberg, A., Erdeniz, N., Cromley, D., Billheimer, J. T., and Sturley, S. L. (2000) *J. Biol. Chem.* 275, 15609-15612
10. Oelkers, P., Cromley, D., Padamsee, M., Billheimer, J. T., and Sturley, S. L. (2002) *J. Biol. Chem.* 277, 8877-8881
11. Dahlqvist, A., Stahl, U., Lenman, M., Banas, A., Lee, M., Sandager, L., Ronne, H., and Stymne, S. (2000) *Proc. Natl. Acad. Sci. U.S.A.* 97, 6487-6492
12. Listenberger, L. L., Han, X., Lewis, S. E., Cases, S., Farese, R. V., Jr., Ory, D. S., and Schaffer, J. E. (2003) *Proc. Natl. Acad. Sci. U.S.A.*, 100, 3077-3082
13. Forsburg, S. L. (1999) *Trends Genet.* 15,340-344
14. Wood, V., Gwilliam, R., Rajandream, M. A., Lyne, M., Lyne, R., Stewart, A., Sgouros, J., Peat, N., Hayles, J., Baker, S., Basham, D., Bowman, S., Brooks, K., Brown, D., Brown, S., Chillingworth, T., Churcher, C., Collins, M., Connor, R., Cronin, A., Davis, P., Feltwell, T., Fraser, A., Gentles, S., Goble, A., Hamlin, N., Harris, D., Hidalgo, J., Hodgson, G., Holroyd, S., Hornsby, T., Howarth, S., Huckle, E. J., Hunt, S., Jagels, K., James, K., Jones, L., Jones, M., Leather, S., McDonald, S., McLean, J., Mooney, P., Moule, S., Mungall, K., Murphy, L., Niblett, D., Odell, C., Oliver, K., ONeil, S., Pearson, D., Quail, M. A., Rabbinowitsch, E., Rutherford, K., Rutter, S., Saunders, D., Seeger, K., Sharp, S., Skelton, J., Simmonds, M., Squares, R., Squares, S., Stevens, K., Taylor, K., Taylor, R. G., Tivey, A., Walsh, S., Warren, T., Whitehead, S., Woodward, J., Volckaert, G., Aert, R., Robben, J., Grymonprez, B., Weltjens, I., Vanstreels, B., Rieger, M., Schafer, M., Muller-Auer, S., Gabel, C., Fuchs, M., Dusterhoft, A., Fritzc, C., Holzer, E., Moestl, D., Hilbert, H., Borzym, K., Langer, I., Beck, A., Lehrach, H., Reinhardt, R., Pohl, T. M., Eger, P., Zimmermann, W., Wedler, H., Wambutt, R., Purnelle, B., Goffeau, A., Cadieu, E., Dreano, S., Gloux, S., Lelaure, V., Mottier, S., Galibert, F., Aves, S. J., Xiang, Z., Hunt, C., Moore, K., Hurst, S. M., Lucas, M., Rochet, M., Gaillardin, C., Tallada, V. A., Garzon, A., Thode, G., Daga, R. R., Cruzado, L., Jimenez, J., Sanchez, M., del, Rey, F., Benito, J., Dominguez, A., Revuelta, J. L., Moreno, S., Armstrong, J., Forsburg, S. L., Cerutti, L., Lowe, T., McCombie, W. R., Paulsen, I., Potashkin, J., Shpakovski, G. V., Ussery, D., Barrell, B. G., Nurse, P., and Cerrutti, L. (2002) *Nature* 415, 871-880
15. Toone, W. M., and Jones, N. (1998) *Genes Cells* 3, 485-498
16. Li, T., Naqvi, N. I., Yang, H., and Teo, T. S. (2000) *Biochem. Biophys. Res. Commun.* 272, 270-275
17. Moreno, S., Klar, A., and Nurse, P. (1991) *Methods Enzymol.* 194, 795-823
18. Prentice, H. L. (1992) *Nucleic Acids Res.* 20, 621
19. Wach, A., Brachat, A., Pohlmann, R., and Philippsen, P. (1994) *Yeast* 10, 1793-1808
20. Craven, R. A., Griffiths, D. J., Sheldrick, K. S., Randall, R. E., Hagan, I. M., and Carr, A. M. (1998) *Gene* (Amst.) 221, 59-68
21. Basi, G., Schmid, B., and Maundrell, K. (1993) *Gene* (Amst.). 123, 131-136
22. Lightner, V. A., Bell, R. M., and Modrich, P. (1983) *J. Biol. Chem.* 258, 10856-10861
23. Kearns, B. G., McGee, T. P., Mayinger, P., Gedvilaite, A., Phillips, S. E., Kagiwada, S., and Bankaitis, V. A. (1997) *Nature* 387, 101-105
24. Fishbein, J. D., Dobrowsky, R. T., Bielawska, A., Garrett, S., and Hannun, Y. A. (1993) *J. Biol. Chem.* 268, 9255-9261
25. Yang, H., Bard, M., Bruner, D. A., Gleeson, A., Deckelbaum, R. J., Aljinovic, G., Pohl, T. M., Rothstein, R., and Sturley, S. L. (1996) *Science* 272, 1353-1356
26. Madeo, F., Frohlich, E., Ligr, M., Grey, M., Sigrist, S., Wolf, D. H., and Frohlich, K. U. (1999) *J. Cell Biol.* 145, 757-767

27. Zinser, E., and Daum, G. (1995) *Yeast* 11, 493-536

28. Greenspan, P., Mayer, E. P., and Fowler, S. D. (1985) *J. Cell Biol.* 100, 965-973

29. Buszczak, M., Lu, X., Segraves, W. A., Chang, T. Y., and Cooley, L. (2002) *Genetics* 160, 1511-1518

30. Gangar, A., Raychaudhuri, S., and Pajasekharan, R. (2002) *Biochem. J.* 365, 577-589

31. Madeo, F., Frohlich, E., and Frohlich, K. U. (1997) *J. Cell Biol.* 139, 729-734

32. Madeo, F., Herker, E., Maldener, C., Wissing, S., Lachelt, S., Herlan, M., Fehr, M., Lauber, K., Sigrist, S. J., Wesselborg, S., and Frohlich, K. U. (2002) *Mol. Cell* 9, 911-917

33. Madeo, F., Engelhardt, S., Herker, E., Lehmann, N., Maldener, C., Proksch, A., Wissing, S., and Frohlich, K. U. (2002) *Curr. Genet.* 41, 208-216

34. Hosaka, K., and Yamashita, S. (1984) *Biochim. Biophys. Acta* 796, 110-117

35. Zheng, Z., and Zou, J. (2001) *J. Biol. Chem.* 276, 41710-41716

36. Alvarez, M. E., Pennell, R. I., Meijer, P. J., Ishikawa, A., Dixon, R. A., and Lamb, C. (1998) *Cell* 92, 773-784

37. Kane, D. J., Sarafian, T. A., Anton, R., Hahn, H., Gralla, B. B., Valentine, 3. S., Ord, T., and Bredesen, D. E. (1993) *Science* 262, 1274-1277

38. Listenberger, L. L., Ory, D. S., and Schaffer, J. E. (2001) *J. Biol. Chem.* 276, 14890-14895

39. Mazzoni, C., Mancini, P., Verdone, L., Madeo, F., Serafini, A., Herker, E., and Falcone, C. (2003) *Mol. Biol. Cell* 14, 721-729

40. Ink, B., Zornig, M., Baum, B., Hajibagheri, N., James, C., Chittenden, T., and Evan, G. (1997) *Mol. Cell. Biol.* 17, 2468-2474

41. James, C., Gschmeissner, S., Fraser, A., and Evan, G. I. (1997) *Curr. Biol.* 7, 246-252

42. Cande, C., Cecconi, P., Dessen, P., and Kroemer, G. (2002) *J. Cell Sci.* 115, 4727-4734

43. Cheng, J., Park, T. S., Chio, L. C., Fischl, A. S., and Ye, X. S. (2003) *Mol. Cell. Biol.* 23, 163-177

44. Werner-Washburne, M., Braun, E. L., Crawford, M. E., and Peck, V. M. (1996) *Mol. Microbiol.* 19, 1159-1166

45. Cross, T. G., Scheel-Toellner, D., Henriquez, N. V., Deacon, E., Salmon, M., and Lord, J. M. (2000) *Exp. Cell Res.* 256, 34-41

46. Perez, P., and Calonge, T. M. (2002) *J. Biochem.* (Tokyo) 132, 513-517

47. Song, Y., Ailenberg, M., and Silverman, M. (1999) *Mol. Biol. Cell* 10, 1609-1619

48. Severin, F. F., and Hyman, A. A. (2002) *Curr. Biol.* 12, R233-R235

49. Lin, A. (2003) *Bioessays* 25, 17-24

50. Bergman, R. N., and Ader, M. (2000) *Trends Endocrinol. Metab.* 11, 351-356

51. Unger, R. H., and Orci, L. (2002) *Biochim. Biophys. Acta* 1585, 202-212

52. Inoguchi, T., Li, P., Umeda, F., Yu, H. Y., Kakimoto, M., Imamura, M., Aoki, T., Etoh, T., Hashimoto, T., Naruse, M., Sano, H., Utsumi, H., and Nawata, H. (2000) *Diabetes* 49, 1939-1945

53. Smith S.J. et al. (2000) *Nat Genet.* 25(1):87-90

54. Chen and Farese, (2000) *Trends Cardiovasc Med.* 10(5):188-92

55. W. I. Sivitz, (2001) *Postgrad Med* 109(4):55-64

---

What is claimed is:

1. An isolated *Schizosaccharomyces pombe* yeast strain comprising non-functional dgal and plhl genes.

2. The yeast strain of claim 1 that is a *Schizosaccharomyces pombe* Δdgal Δplhl double deletion mutant.

3. The yeast strain of claim 1 comprising an exogenous gene that, when expressed in the *Schizosaccharomyces* yeast strain, results in triacylglycerol synthesis.

4. The yeast strain of claim 3 wherein the exogenous gene is a diacylglycerol acyl-transferase gene.

5. The yeast strain of claim 4 wherein the diacylglycerol acyl-transferase gene is a human diacylglycerol acyl-transferase gene.

6. A method for screening or identifying a compound that inhibits or prevents TAG synthesis, comprising: treating with a compound a culture of a fission yeast strain comprising non-functional dgal and plhl genes, wherein the yeast strain comprises an exogenous gene which is expressible in the yeast strain and which, when-expressed in the yeast strain, results in TAG synthesis; and detecting any TAG synthesis in the culture.

7. The method of claim 6 wherein the yeast strain is a *Schizosaccharomyces pombe* Δdga1 Δplh1 double deletion mutant.

8. The method of claim 6 wherein the exogenous gene is a diacylglycerol acyl-transferase gene.

9. The method of claim 8 wherein the diacylglycerol acyl-transferase gene is a human diacylglycerol acyl-transferase gene.

10. The method of claim 6 wherein the compound is a small molecule, a protein, a peptide, an antibody, a hormone, a lipid or a nucleic acid.

11. The method of claim 6 wherein the compound is useful for treatment of obesity, diabetes, coronary heart disease, heart failure or cardiomyopathy.

12. The method of claim 6 wherein the detecting comprises adding labeled substrate of TAG synthesis to the culture.

13. The method of claim 12 wherein the substrate is labeled with a radioactive molecule, a chemiluminescent molecule, a fluorescent molecule, an enzyme that cleaves a reagent to produce a coloured molecule, a coloured molecule or a heavy metal complex.

14. The method of claim 12 wherein the labeled substrate is a fatty acid.

15. The method of claim 14 wherein the fatty acid is oleic acid or palmitic acid.

16. The method of claim 12 wherein the detecting comprises extraction of cellular lipids and separation of the cellular lipids by thin layer chromatography.

17. The method of claim 6 wherein the detecting comprises exposing the culture to conditions that are suitable for inducing lipoapoptosis in a culture not expressing the exogenous gene and detecting lipoapoptosis in the exposed culture.

18. The method of claim 17 wherein the exposing comprises addition of fatty acid or diacylglycerol to the culture or to nutrient starvation.

19. The method of claim 18 wherein the fatty acid or diacylglycerol is added to a liquid culture during log phase.

20. The method of claim 17 wherein the fatty acid is oleic acid or palmitic acid and the diacylglycerol is diC8 diacylglycerol.

21. The method of claim 20 wherein the palmitic acid is added at a concentration of about 1 mM.

22. The method of claim 18 wherein the nutrient starvation comprises culturing the culture in water or low-glucose medium.

23. The method of claim 17 wherein the detecting lipoapoptosis comprises measuring cell viability.

24. The method of claim 17 wherein the detecting lipoapoptosis comprises detecting an apoptotic marker.

25. The method of claim 24 wherein the apoptotic marker is fragmented nuclear DNA, exposed phosphatidyl serine at the outer leaflet of the plasma membrane or production of reactive oxygen species.

26. The method of claim 24 wherein the detecting lipoapoptosis comprises adding a detection molecule.

27. The method of claim 26 wherein the detection molecule is a radioactive molecule, a chemiluminescent molecule, a fluorescent molecule, an enzyme that cleaves a reagent to produce a coloured molecule, a coloured molecule or a heavy metal complex.

28. A method of screening or identifying a compound that inhibits lipotoxicity, comprising: treating with a compound a culture of a fission yeast strain comprising non-functional dga1 and plh1 genes; exposing the treated culture to conditions that are suitable for inducing lipotoxicity in an untreated culture; and detecting lipotoxicity in the treated culture.

29. The method of claim 28 wherein lipotoxicity is lipoapoptosis.

30. The method of claim 28 wherein the yeast strain is a *Schizosaccharomyces pombe* Adga1 Aplh1 double deletion mutant.

31. The method of claim 28 wherein the compound is a small molecule, a protein, a peptide, an antibody, a hormone, a lipid or a nucleic acid.

32. The method of claim 28 wherein the compound is useful for treatment of obesity, diabetes, coronary heart disease, heart failure or cardiomyopathy.

33. The method of claim 28 wherein the exposing the treated culture comprises addition of fatty acid or diacylglycerol to the culture or nutrient starvation.

34. The method of claim 33 wherein the fatty acid or diacylglycerol is added to a liquid culture during log phase.

35. The method of claim 33 wherein the fatty acid is oleic acid or palmitic acid and the diacylglycerol is diC8 diacylglycerol.

36. The method of claim 35 wherein the palmitic acid is added to a concentration of about 1 mM.

37. The method of claim 36 wherein the nutrient starvation comprises culturing the treated culture in water or low-glucose medium.

38. The method of claim 29 wherein the detecting comprises detecting an apoptotic marker.

39. The method of claim 38 wherein the apoptotic marker is fragmented nuclear DNA, exposed phosphatidyl serine at the outer leaflet of the plasma membrane or production of reactive oxygen species.

40. The method of claim 38 wherein the detecting lipoapoptosis comprises adding a detection molecule.

41. The method of claim 40 wherein the detection molecule is a radioactive molecule, a chemiluminescent molecule, a fluorescent molecule, an enzyme that cleaves a reagent to produce a coloured molecule, a coloured molecule or a heavy metal complex.

42. The method of claim 29 wherein the detecting comprises measuring cell viability.

43. The method of claim 42 wherein measuring cell viability comprises performing a colony forming assay.

44. A method of making a fission yeast strain comprising non-functional dga1 and plh1 genes, comprising functionally interrupting the dga1 and plh1 genes in a fission yeast strain.

45. A method of screening or identifying a gene that complements non-functional dga1 and plh1 genes, comprising transforming a fission yeast strain comprising non-functional dga1 and plh1 genes with an exogenous gene; culturing the transformed yeast strain; and detecting any TAG synthesis in the culture.

46. A kit or commercial package comprising a fission yeast strain comprising non-functional dga1 and plh1 genes and instructions for screening or identifying a compound that inhibits TAG synthesis.

47. A kit or commercial package comprising a fission yeast strain comprising non-functional dga1 and plh1 genes and instructions for screening or identifying a compound that inhibits lipotoxicity.

48. A kit or commercial package comprising a fission yeast strain comprising non-functional dga1 and plh1 genes and instructions for screening or identifying a gene that complements the dga1 and plh1 genes.

* * * * *